US012251352B2

(12) United States Patent
Liu et al.

(10) Patent No.: US 12,251,352 B2
(45) Date of Patent: Mar. 18, 2025

(54) SYSTEM, APPARATUS, AND METHOD FOR CONTROLLING A DEVICE BASED ON DISTANCE

(71) Applicant: HYTTO PTE. LTD., Singapore (SG)

(72) Inventors: Dan Liu, Guangdong (CN); Jilin Qiu, Guangdong (CN)

( * ) Notice: Subject to any disclaimer, the term of this patent is extended or adjusted under 35 U.S.C. 154(b) by 0 days.

(21) Appl. No.: 17/812,602

(22) Filed: Jul. 14, 2022

(65) Prior Publication Data
US 2022/0347046 A1    Nov. 3, 2022

Related U.S. Application Data

(63) Continuation-in-part of application No. 17/717,917, filed on Apr. 11, 2022, now Pat. No. 11,938,078, and a continuation-in-part of application No. 17/520,889, filed on Nov. 8, 2021, and a continuation-in-part of application No. 16/835,808, filed on Mar. 31, 2020, now Pat. No. 11,452,669, said application No. 17/717,917 is a continuation of application No. 16/352,876, filed on Mar. 14, 2019, now Pat. No. 11,311,453.

(60) Provisional application No. 62/830,195, filed on Apr. 5, 2019.

(51) Int. Cl.
*A61H 19/00* (2006.01)
*A61F 5/41* (2006.01)
*A61H 23/02* (2006.01)

(52) U.S. Cl.
CPC .............. *A61H 19/44* (2013.01); *A61F 5/41* (2013.01); *A61H 19/34* (2013.01); *A61F 2005/417* (2013.01); *A61H 23/02* (2013.01); *A61H 2201/5007* (2013.01); *A61H 2201/5071* (2013.01); *A61H 2201/5097* (2013.01)

(58) Field of Classification Search
CPC .......... A61F 5/41; A61H 19/00; A61H 19/34; A61H 19/44; A61H 2201/5007; A61H 2201/5012; A61H 2201/5097
See application file for complete search history.

(56) References Cited

U.S. PATENT DOCUMENTS

| | | | |
|---|---|---|---|
| 3,361,130 A | 1/1968 | Rowe | |
| 5,807,287 A | 9/1998 | Cheng | |
| 6,277,085 B1 | 8/2001 | Flynn | |
| 6,368,268 B1 | 4/2002 | Sandvick et al. | |
| 6,695,770 B1 * | 2/2004 | Choy | A61H 19/32 600/38 |

(Continued)

FOREIGN PATENT DOCUMENTS

| | | |
|---|---|---|
| KR | 101256565 B1 | 4/2013 |
| WO | 2006040750 A1 | 4/2006 |

(Continued)

*Primary Examiner* — Christine H Matthews
(74) *Attorney, Agent, or Firm* — Keefe IP Law, PLLC

(57) ABSTRACT

A system is disclosed. The system includes an accessory control module, comprising computer-executable code stored in non-volatile memory, a processor, an accessory of a user, and a terminal device. The accessory control module, the processor, the accessory, and the terminal device are configured to determine a distance between the terminal device and either the accessory or a user device of the user, and control the accessory to perform a predetermined action for sexually stimulating the user based on the distance.

15 Claims, 10 Drawing Sheets

(56) References Cited

U.S. PATENT DOCUMENTS

| | | |
|---|---|---|
| 8,255,299 B2 | 8/2012 | Cambridge |
| 8,644,967 B2 | 2/2014 | Seiler |
| 8,936,544 B2 | 1/2015 | Shahoian et al. |
| 9,762,515 B1 | 9/2017 | Olivares et al. |
| 10,051,328 B2 | 8/2018 | Olivares, II et al. |
| 10,218,795 B1 | 2/2019 | Messinger |
| 10,576,013 B1 | 3/2020 | Sloan |
| 11,134,041 B1 | 9/2021 | He |
| 2002/0065477 A1 | 5/2002 | Boyd et al. |
| 2002/0133103 A1 | 9/2002 | Williams et al. |
| 2003/0036678 A1 | 2/2003 | Abbassi |
| 2004/0082831 A1 | 4/2004 | Kobashikawa et al. |
| 2004/0097852 A1 | 5/2004 | Boyd et al. |
| 2005/0138560 A1 | 6/2005 | Lee et al. |
| 2006/0247561 A1 | 11/2006 | Chiu |
| 2012/0259171 A1 | 10/2012 | Shmakov |
| 2012/0304216 A1 | 11/2012 | Strong |
| 2013/0165747 A1 | 6/2013 | Maggs |
| 2014/0011557 A1 | 1/2014 | Coyle |
| 2014/0155690 A1 | 6/2014 | Morton |
| 2016/0049043 A1 | 2/2016 | Tennenhaus et al. |
| 2017/0095207 A1 | 4/2017 | Thomas et al. |
| 2017/0119619 A1 | 5/2017 | Dills |
| 2018/0116904 A1 | 5/2018 | Lieberman et al. |
| 2018/0168919 A1* | 6/2018 | Fung ............... A61H 23/02 |
| 2019/0133877 A1 | 5/2019 | Cambridge |
| 2020/0009009 A1 | 1/2020 | Nishida |
| 2020/0276504 A1 | 9/2020 | Liu |
| 2020/0289363 A1 | 9/2020 | Liu |
| 2020/0315908 A1 | 10/2020 | Liu |
| 2020/0366972 A1 | 11/2020 | Sloan |
| 2021/0341992 A1 | 11/2021 | Cambridge |
| 2022/0104996 A1* | 4/2022 | Bennett ............ A61H 19/30 |
| 2022/0141550 A1 | 5/2022 | Liu |

FOREIGN PATENT DOCUMENTS

| | | |
|---|---|---|
| WO | 2008067487 A2 | 6/2008 |
| WO | 2015009626 A1 | 1/2015 |

* cited by examiner

SYSTEM, APPARATUS, AND METHOD FOR CONTROLLING A DEVICE BASED ON DISTANCE

CROSS REFERENCE TO RELATED APPLICATIONS

This application is a continuation-in-part of U.S. patent application Ser. No. 17/520,889, filed Nov. 8, 2021. This application is also a continuation-in-part of U.S. patent application Ser. No. 17/717,917, filed Apr. 11, 2022, which is a continuation of U.S. patent application Ser. No. 16/352,876, filed Mar. 14, 2019 (now U.S. Pat. No. 11,311,453 issued on Apr. 26, 2022). This application is also a continuation-in-part of U.S. patent application Ser. No. 16/835,808, filed Mar. 31, 2020, which claims priority to U.S. Provisional Patent Application No. 62/830,195, filed Apr. 5, 2019. Each of the above applications is hereby incorporated by reference in its entirety.

FIELD OF THE INVENTION

The present disclosure generally relates to a system, apparatus, and method for controlling a device, and more particularly to a system, apparatus, and method for controlling a device based on distance.

BACKGROUND OF THE INVENTION

Conventional systems exist for controlling a device such as an adult toy. Such systems may include controlling an adult toy using a user device such as, for example, a tablet, a smartphone, or other type of device. These systems may also include control of imaging devices for providing images of a model such as a human model to a viewer.

However, conventional systems do not adequately provide for a control of an adult toy based on an environment in which such devices may be used.

Accordingly, a need in the art exists for an efficient technique for controlling devices such as adult toys to effectively account for the environment in which the devices are located.

The exemplary disclosed system and method are directed to overcoming one or more of the shortcomings set forth above and/or other deficiencies in existing technology.

SUMMARY OF THE INVENTION

In one exemplary aspect, the present disclosure is directed to a system. The system includes an accessory control module, comprising computer-executable code stored in non-volatile memory, a processor, an accessory of a user, and a terminal device. The accessory control module, the processor, the accessory, and the terminal device are configured to determine a distance between the terminal device and either the accessory or a user device of the user, and control the accessory to perform a predetermined action for sexually stimulating the user based on the distance.

In another aspect, the present disclosure is directed to a method. The method includes providing an accessory of a user, providing a terminal device, wirelessly transmitting and receiving signals using the accessory and the terminal device, determining a distance between the terminal device and either the accessory or a user device of the user, and controlling the accessory to perform a predetermined action for sexually stimulating the user based on the distance.

DETAILED DESCRIPTION AND INDUSTRIAL APPLICABILITY

Figure 1:
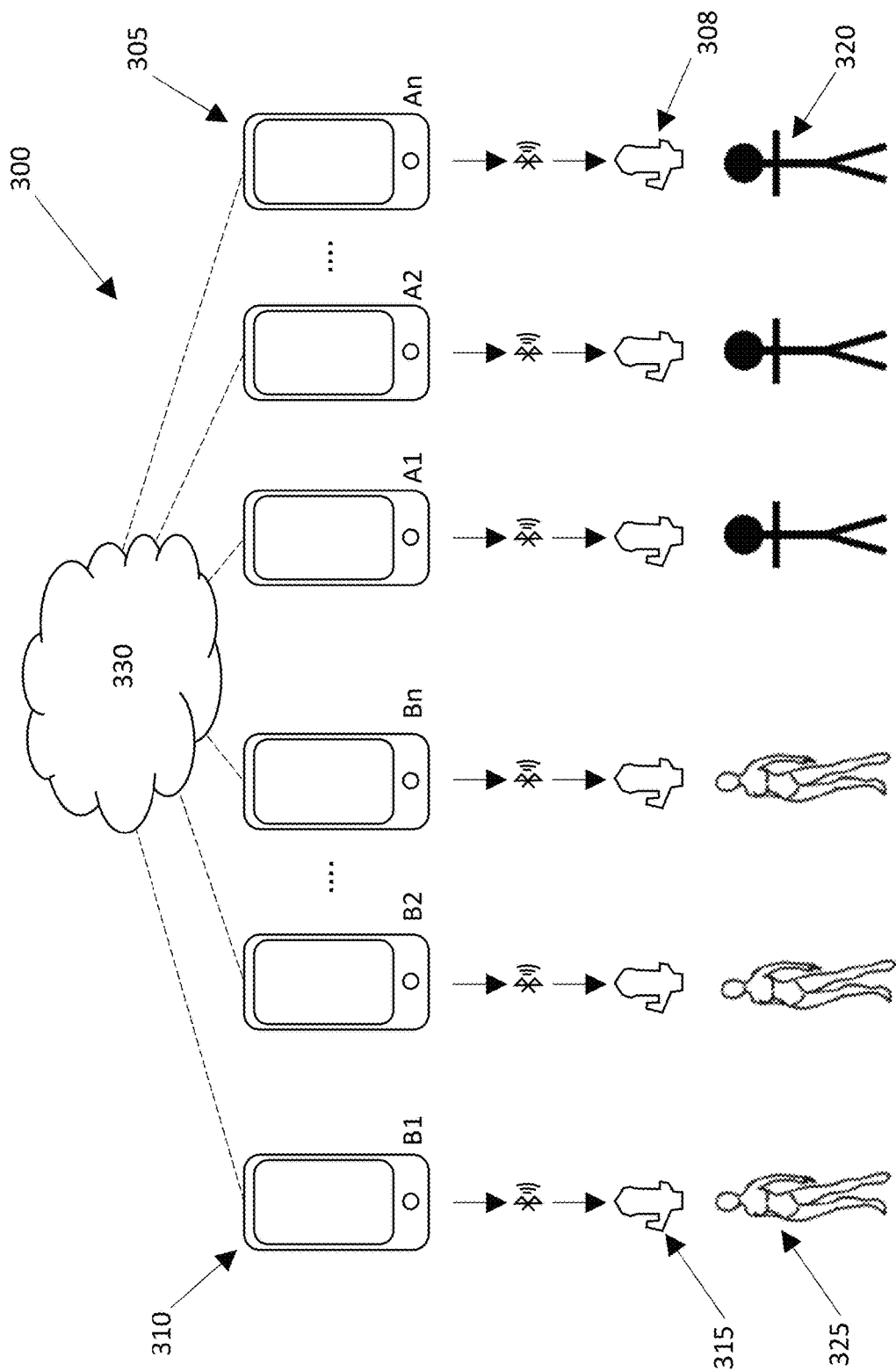
FIG. 1 is a schematic illustration of an exemplary system of the present invention.

FIG. 1 illustrates an exemplary system 300 for controlling devices. In at least some exemplary embodiments, system 300 may be a system for controlling a sexual stimulation device, using an alarm, in real-time (e.g., in real-time or in near real-time) for an adult entertainment application. In at least some exemplary embodiments, system 300 may include a smart sex toy that may be remotely controlled, for example, by a physical remote, an application (e.g., APP) on the phone, sound or music, motion of a wireless-connected device (e.g., phone) for example as described herein. System 300 may include a device such as a sex toy or adult toy that may be controlled as a function of a control pattern, remotely controlled, controlled based on distance (e.g., location or proximity), intensity (e.g., vibration intensity), and/or virtual reality. System 300 may operate to control an adult toy based on distance (e.g., distance between accessories and/or devices of users).

As illustrated in FIG. 1, system 300 may include one or more user devices 305, one or more model devices 310, one or more viewer accessories 308, and one or more model accessories 315. For example, system 300 may include a plurality of user devices 305, a plurality of viewer accessories 308, a plurality of model devices 310, and a plurality of model accessories 315. Data such as image data, audio data, and/or control data may be transferred between user devices 305, viewer accessories 308, model devices 310, and model accessories 315.

As illustrated in FIG. 1, system 300 may include any desired number of user devices 305 (e.g., A1, A2, ... An). User device 305 may be any suitable device for interfacing with other components of system 300 such as a computing device (e.g., user interface). For example, user device 305 may be any suitable user interface for receiving input and/or providing output (e.g., image data) to a user 320. User device 305 may include a camera and a microphone. User device 305 may be, for example, a touchscreen device (e.g., of a smartphone, a tablet, a computer, a smartboard, a virtual reality device, and/or any suitable computer device), a wearable device, a computer keyboard and monitor (e.g., desktop or laptop), an audio-based device for entering input and/or receiving output via sound, a tactile-based device for entering input and receiving output based on touch or feel, a dedicated user interface designed to work specifically with other components of system 300, and/or any other suitable user interface (e.g., including components and/or configured to work with components described below regarding FIGS. 10 and 11). For example, user device 305 may include a touchscreen device of a smartphone or handheld tablet. For example, user device 305 may include a display (e.g., a computing device display, a touchscreen display, and/or any other suitable type of display) that may provide output, image data, and/or any other desired output or input prompt to a user. For example, the exemplary display may include a graphical user interface to facilitate entry of input by a user and/or receiving output such as image data. An application for example as described herein and/or a web browser may be installed on user device 305 and utilized by user 320. User device 305 may include storage for example as described regarding FIG. 10. For example, user device 305 may have storage for storing programming instructions for example as described below.

Figure 2:
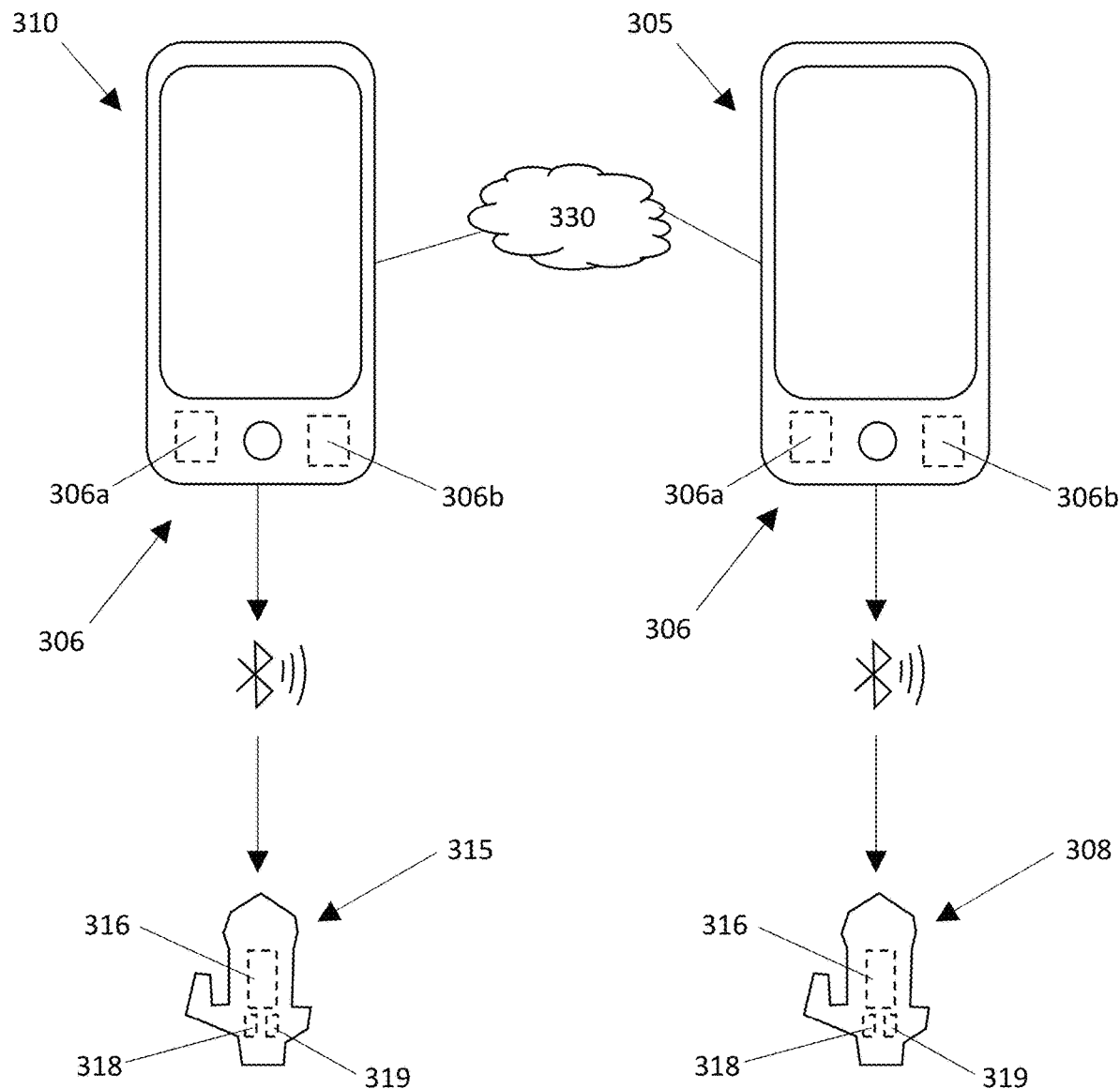
FIG. 2 is a schematic illustration of an exemplary system of the present invention.

As illustrated in FIG. 2, user device 305 may include a sensor array 306. In at least some exemplary embodiments, sensor array 306 may include one or more sensors integrated or built into the exemplary disclosed user device (e.g., user device 305) such as, for example, a mobile phone, a pad, or a wearable device. Sensor array 306 may include any suitable sensors for use with system 300 such as, for example, a location sensor 306a and a movement sensor 306b. Location sensor 306a may include a GPS device, a Galileo™ device, a GLONASS™ device, an IRNSS device, a BeiDou™ device, and/or any other suitable device that may operate with a global navigation system.

Movement sensor 306b may include any suitable components for sensing motion (e.g., motion amplitude), velocity, and/or acceleration. Movement sensor 306b may include an acceleration sensor. Movement sensor 306b may include a gyroscope. For example, movement sensor 306b may include a displacement sensor, a velocity sensor, and/or an accelerometer. For example, movement sensor 306b may include components such as a servo accelerometer, a piezoelectric accelerometer, a potentiometric accelerometer, and/or a strain gauge accelerometer. Movement sensor 306b may include a piezoelectric velocity sensor or any other suitable type of velocity or acceleration sensor.

System 300 may include any desired number of model devices 310 (e.g., B1, B2, . . . Bn). Model device 310 may be similar to user device 305. For example, model device 310 may be any suitable user interface for receiving input and/or providing output (e.g., image data) to a model 325. Model 325 (e.g., a specific user) may operate model device 310 (e.g., a specific user device) to record and transfer image (e.g., video) and audio data to one or more users 320 via a network 330.

Model accessory 315 may be any suitable accessory for use by model 325 (e.g., when model 325 is imaged by model device 310). For example, model accessory 315 may be a prop that is used by model 325 while model 325 is being imaged (e.g., a video or pictures of model 325 are being recorded and/or transmitted in real-time to be viewed by user 320). For example, model accessory 315 may be a device used for erotic stimulation (e.g., a sex aid or a "sex toy"). Model accessory 315 may be a sexual simulation device that may be associated with a given model 325 (e.g., a specific user) and respective model device 310 (e.g., a specific user device) of that given model 325. In at least some exemplary embodiments, model accessory 315 may be a massaging apparatus for human genitalia (e.g., a vibrator). For example, model accessory 315 may be any suitable device for use in a video or pictures recorded by model device 310, which may be an erotic video or erotic pictures). In at least some exemplary embodiments, model accessory 315 may be a tool or other indicator that may be used in video or pictures recorded by model device 310 such as surveying equipment, a sign providing information such as location or time information, a surveillance tool used by model 325, and/or any other suitable tool or accessory that may be used while model device 310 is recording a video or pictures of model 325. For example, model 325 may be an erotic model using model accessory 315 that may be an erotic device, a technician or laborer using model accessory 315 that may be a tool or work device specific to a desired application, an operative using model accessory 315 that may be a surveillance tool or a part of a weapon system being recorded by model device 310, and/or any other desired role using any suitable model accessory 315.

Model accessory 315 may include a motor 316. Motor 316 may include an electric motor. Motor 316 may include a server motor, a stepper motor, a brushless motor, or any other suitable type of motor. Motor 316 may include any suitable vibration motor or haptic motor such as, for example, a mini vibrator motor. Motor 316 may include a low voltage motor. Motor 316 may include a pager motor or a coin vibration motor. Motor 316 may include a linear resonant actuator or an eccentric rotating mass vibration motor. Motor 316 may be powered by any suitable power source, such as a battery (e.g., a nickel-metal hydride battery, a lithium-ion battery, an ultracapacitor battery, a lead-acid battery, and/or a nickel cadmium battery), an electric power source (e.g., a transformer connected to a plug that may plug into an outlet), and/or any other suitable energy source. Model accessory 315 may include a controller 319 that may be any suitable computing device for controlling an operation of motor 316 and a communication device 318. Controller 319 may, for example, include components similar to the components described below regarding FIG. 10. Controller 319 may include for example a processor (e.g., micro-processing logic control device) or board components. Controller 319 may control motor 316 based on input data and/or commands received from user device 305 and/or model device 310 via network 330 and/or a communication device 318 (e.g., transferred directly to communication device 318 by any suitable component of system 300). Motor 316 may be controlled by controller 319 to vibrate model accessory 315 at a desired level or strength, perform a suction operation at a desired level or strength using model accessory 315 (e.g., using model accessory 315 as a suction device), rotate or swing model accessory 315 at a desired speed or amount, contract or expand model accessory 315 by a desired amount, cause model accessory 315 to perform an inhalation action, and/or cause model accessory 315 to perform any other suitable action or function. Controller 319 may include storage for example as described regarding FIG. 10. For example, controller 319 may have storage for storing programming instructions for example as described below.

In at least some exemplary embodiments, motor 316 may be or may include a thermal device such as a heater. In at least some exemplary embodiments, motor 316 may include an electric heating device such as an electric resistance heating device. Motor 316 may include a polyimide heater, a silicone rubber heater, and/or a resistive wire heater. Motor 316 may be controlled by controller 319 to heat or emit heat or warmth from model accessory 315. For example, motor 316 may cause a temperature variation of model accessory 315.

Viewer accessory 308 may be similar to model accessory 315. Viewer accessory 308 may be a sexual simulation device that may be associated with a given user 320 (e.g., a viewer of one or more models 325) and respective user device 305 (e.g., a viewer device) of that given user 320.

Network 330 may be any suitable communication network over which data may be transferred between one or more user devices 305, one or more viewer accessories 308, one or more model devices 310, and/or one or more model accessories 315. Network 330 may be the internet, a LAN (e.g., via Ethernet LAN), a WAN, a WiFi network, or any other suitable network. Network 330 may be similar to WAN 201 described below. The components of system 300 may also be directly connected (e.g., by wire, cable, USB connection, and/or any other suitable electro-mechanical connection) to each other and/or connected via network 330. For example, components of system 300 may wirelessly transmit data by any suitable technique such as, e.g., wirelessly transmitting data via 4G LTE networks (e.g., or 5G networks) or any other suitable data transmission technique for example via network communication. Components of system 300 may transfer data via the exemplary techniques described below regarding FIG. 11. User devices 305, viewer accessories 308, model devices 310, and/or model accessories 315 may include any suitable communication components for communicating with other components of system 300 using for example the communication techniques described above. For example, user devices 305 and model devices 310 may include integrally formed communication devices (e.g., smartphone components), and viewer accessories 308 and model accessories 315 may each include communication device 318 that may communicate using any of the exemplary disclosed communication techniques.

In at least some exemplary embodiments, a given model accessory 315 may communicate with a given model device 310 (e.g., a paired model device 310) via any suitable short distance communication technique. For example, model accessories 315 (e.g., via communication device 318) and model devices 310 may communicate via WiFi, Bluetooth®, ZigBee™, NFC, IrDA, and/or any other suitable short distance technique. Model accessory 315 may be an adult toy that may be connected with model device 310 through short distance wireless communication. An application (e.g., operating using the exemplary disclosed modules) may be installed on model device 310, the application and model device 310 being configured to send commands to model accessory 315 to drive (e.g., actuate) model accessory 315. Viewer accessory 308 may communicate with user device 305 similarly to the communication of model accessory 315 and model device 310 described above.

System 300 may include one or modules for performing the exemplary disclosed operations. The one or more modules may include an accessory control module for controlling viewer accessory 308 and model accessory 315. The one or more modules may be stored and operated by any suitable components of system 300 (e.g., including processor components) such as, for example, network 330, user device 305, viewer accessory 308, model device 310, model accessory 315, and/or any other suitable component of system 300. For example, system 300 may include one or more modules having computer-executable code stored in non-volatile memory. System 300 may also include one or more storages (e.g., buffer storages) that may include components similar to the exemplary disclosed computing device and network components described below regarding FIGS. 10 and 11. For example, the exemplary disclosed buffer storage may include components similar to the exemplary storage medium and RAM described below regarding FIG. 10. The exemplary disclosed buffer storage may be implemented in software and/or a fixed memory location in hardware of system 300. The exemplary disclosed buffer storage (e.g., a data buffer) may store data temporarily during an operation of system 300.

Figure 3:
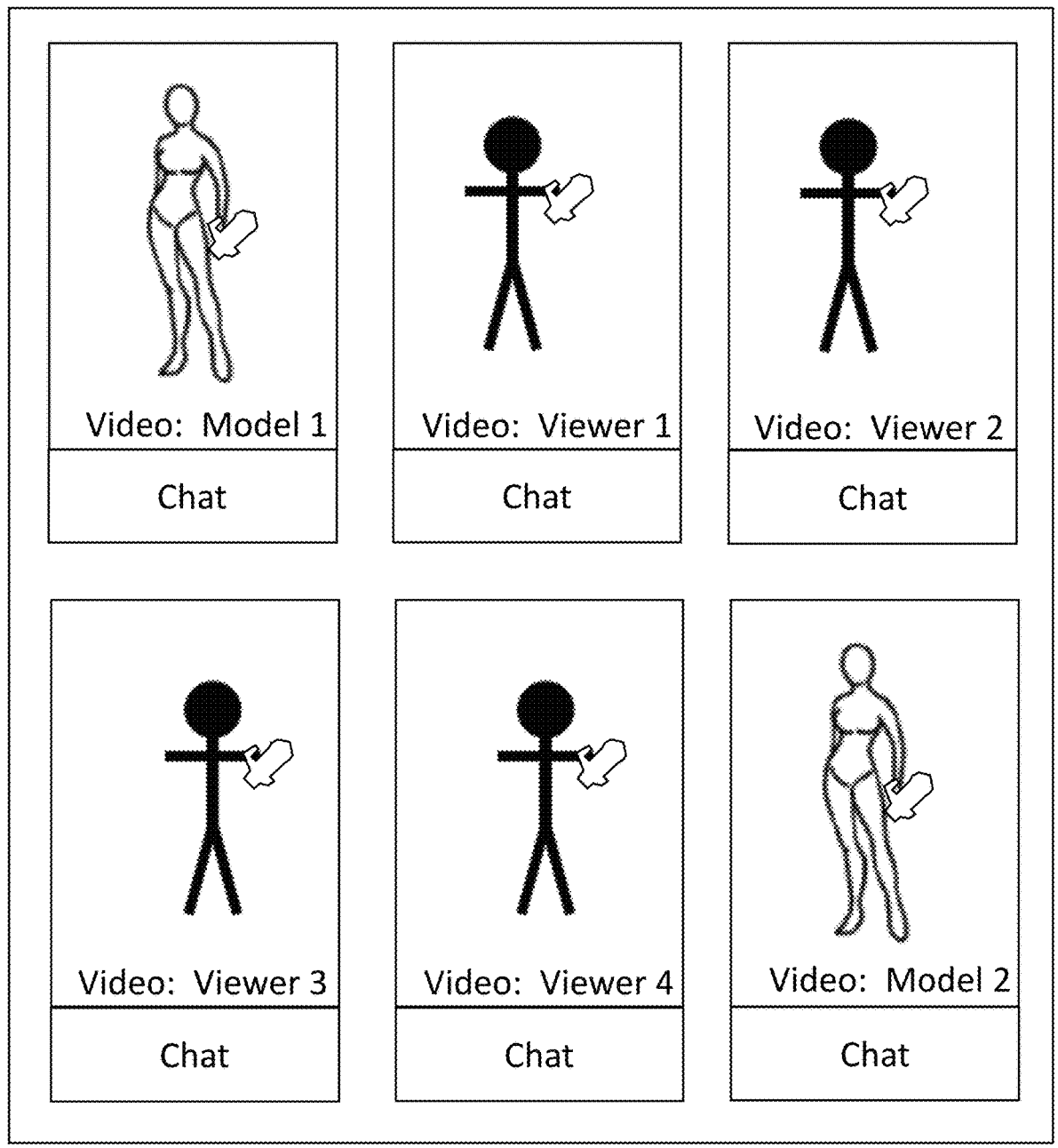
FIG. 3 is a schematic illustration of an exemplary system of the present invention.

The one or more exemplary disclosed modules may also provide a chat room interface via user device 305 and model device 310 for use by each user 320 and model 325. For example, video display of model 325, one or more users 320, and/or and a chat or messaging app (e.g., any suitable chat communication or messaging app such as, for example, text, voice, and/or video chat boxes) may be displayed to each user 320 via user device 305 and to each model 325 via model device 310. One or more users 320 and one or more models 325 may thereby view and chat (e.g., text, voice, and/or video chat) with each other via the one or more exemplary disclosed modules via respective user devices 305 and model devices 310. Each user 320 may thereby view, interact with, and/or chat (e.g., text, voice, and/or video chat) with one or more models 325 and/or other users 320. Also, each model 325 may thereby view, interact with, and/or chat with one or users 320 and/or other models 325. For example, multiple text, voice, and/or video chat boxes including a plurality of users 320 (e.g., viewers each having one or more viewer accessories 308) and/or a plurality of models 325 (e.g., each having one or more model accessories 315) may be displayed to each user 320 and each model 325 via respective user devices 305 and model devices 310. Users 320 and models 325 may thereby view and interact with other users 320 and models 325 that may each have one or more respective accessories (e.g., respective viewer accessories 308 and model accessories 315). FIG. 3 schematically illustrates an exemplary embodiment of the exemplary disclosed chat room that may be displayed to user 320 via user device 305 or to model 325 via model device 310.

The exemplary disclosed system, apparatus, and method may be used in any suitable telecommunications application. The exemplary disclosed system, apparatus, and method may be used in any suitable application for controlling a device such as an adult toy. The exemplary disclosed system, apparatus, and method may be used in any suitable application for using devices such as sexual stimulation devices. For example, the exemplary disclosed system, apparatus, and method may be used in any suitable application for providing entertainment based on using an adult toy. The exemplary disclosed system, apparatus, and method may be used in any suitable telecommunication application for adult entertainment.

Figure 4:
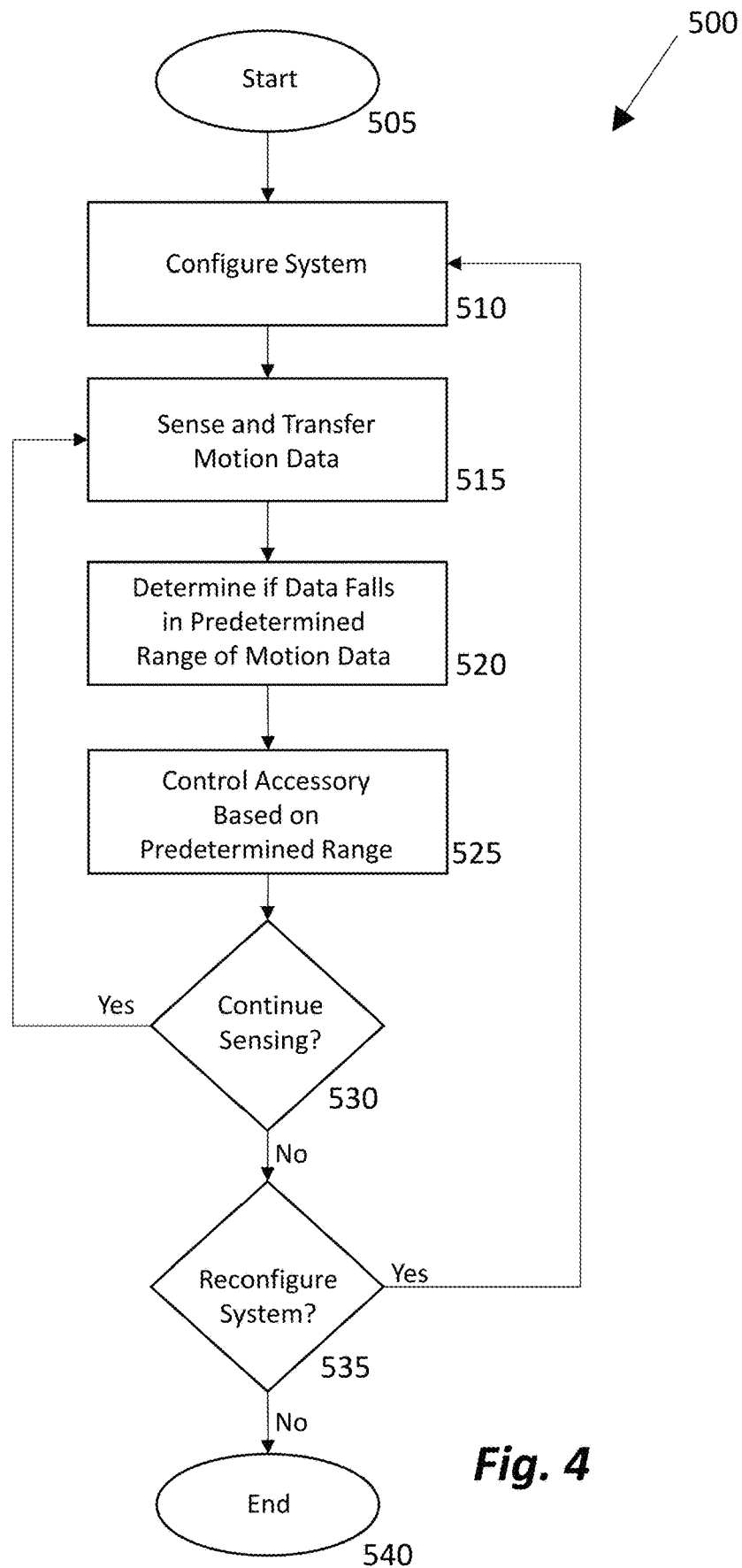
FIG. 4 is a flowchart showing an exemplary process of the present invention.

An exemplary operation of the exemplary disclosed system, apparatus, and method will now be described. For example, FIG. 4 illustrates an exemplary process 500 of system 300. Process 500 begins at step 505.

At step 510, system 300 may be configured. For example, system 300 may be configured as illustrated in FIGS. 1 and 2 or with any other suitable configuration. Any desired number and arrangement of user devices 305, accessories 308, model devices 310, and accessories 315 may be provided in system 300. In at least some exemplary embodiments, system 300 may be a system that operates based on real-time motion of a user device (e.g., user device 305) for use in adult entertainment. For example, system 300 may sense and transfer data, process data, and control accessory 315 (e.g., and/or accessory 308) in real-time or in near real-time based on real-time (e.g., or near real-time) motion of user device 305 (e.g., and/or based on motion of model device 310 in at least some exemplary embodiments). Accessory 315 and/or accessory 308 (e.g., an operable adult toy) may be configured to receive data and signals from other components of system 300 for example as described herein. The exemplary disclosed module, storage (e.g., storage buffer), and hardware may include a memory having stored thereon instructions, a processor configured to execute the instructions resulting in a software application, and a software application configured to perform process 500.

In at least some exemplary embodiments, system 300 may include an accessory control module, comprising computer-executable code stored in nonvolatile memory, a processor, a user device including at least one sensor, and an accessory for a human model, the accessory including a motor or a heater. The accessory control module, the processor, the user device, and the accessory may be configured to sense a velocity or an acceleration of the user device using the at least one sensor, determine if the sensed velocity or the sensed acceleration falls within at least one range of a plurality of predetermined ranges, and control the motor or the heater to drive a predetermined action of the accessory based on the at least one range.

In at least some exemplary embodiments at step 510, user 320 may install an application of system 300 on user device 305 (e.g., and/or model 325 may install the application on model device 310). User 320 (e.g., and/or model 325) may authorize the application to access the data of sensor array 306 (e.g., an acceleration sensor and a GPS) of user device 305 (e.g., and/or model device 310). User 320 (e.g., and/or model 325) may also authorize the application to access the data of Bluetooth® or any other suitable communication components of user device 305 (e.g., and/or model device 310). Model 325 (e.g., and/or user 320) may also connect accessory 315 to model device 310 (e.g., and/or user device 305) via Bluetooth® or any other suitable communication technique.

At step 515, system 300 may operate to sense and transfer motion data. One or more models 325 may initiate communication (e.g., start a chat session) using model devices 310 with one or more users 320 using user devices 305 (e.g., or one or more users 320 may initiate communication with one or more models 325). For example, users 320 and models 325 may chat using the exemplary disclosed modules (e.g., applications) described herein. Model 325 utilizing model device 310 may receive and approve a request (e.g., a toy control request) sent by user 320 utilizing user device 305, the request if approved allowing user 320 to control accessory 315 operated by model 325 for example as described herein. System 300 may detect motion data (e.g., a real-time motion amplitude) of the exemplary disclosed device (e.g., user device 305), the motion amplitude including movement speed and movement acceleration of the device. Location sensor 306a may sense position data of user device 305 (e.g., and/or model device 310). Movement sensor 306b may sense acceleration and/or velocity data of user device 305 (e.g., and/or model device 310). User device 305 (e.g., and/or model device 310) may transfer the sensed motion data of location sensor 306a and movement sensor 306b to any desired component of system 300 (e.g., to network 330 or any other components of system 300 including the exemplary disclosed modules, storage, and/or processors).

In at least some exemplary embodiments and at step 515, system 300 may be configured (e.g., the exemplary disclosed one or more modules may be configured) to define (e.g., set up or to have) one or more ranges of rewards. Rewards may be a tip or virtual currency that may be purchased or credited to a user (e.g., user 320) using any suitable payment technique. Rewards may be awarded from user 320 to model 325 based on a performance of model 325 viewed by user 320 (e.g., adult entertainment). An application of system 300 operating based on the exemplary disclosed modules may be configured to receive reward messages or data from external devices (e.g., user device 305 and/or any other suitable external device). The reward messages or data may include a reward amount. System 300 may determine whether the reward (e.g., reward data) falls into one or more predetermined reward ranges (e.g., reward amount ranges). The one or more predetermined reward amount ranges may correspond to the exemplary disclosed predetermined ranges described at step 520. If a reward (e.g., a tip) falls within one or more predetermined reward amount ranges, accessory 315 may be controlled for example as described at step 525.

At step 520, system 300 may operate to determine whether the magnitude of the motion data (e.g., motion amplitude) is within a predetermined range or one or more of a plurality of predetermined ranges (e.g., falls within one or more preset motion amplitude parameters). For example, the motion amplitude parameters may include one or more ranges of motion amplitude and/or actions (e.g., as described herein) corresponding or correlating to each of the one or more ranges. The exemplary disclosed modules, storage, and/or processors that may be integrated with user device 305, network 330, and/or any other suitable component of system 300 may determine whether the sensed motion data falls within one or more of the exemplary disclosed plurality of ranges. A predefined action or function of accessory 315 and/or accessory 308 (e.g., for example as described at step 525) may be associated with each of the plurality of predetermined ranges. In at least some exemplary embodiments, the exemplary disclosed predetermined ranges may correspond to the exemplary disclosed rewards described above.

In at least some exemplary embodiments, the plurality of predetermined ranges may be a plurality of speed mode parameters of one or more ranges. The speed mode parameters may correspond to a plurality of transportation modes (e.g., traffic patterns) having one or more general speeds or speed ranges corresponding to each of the transportation modes. The transportation modes (e.g., traffic patterns) may include a walking mode having a speed range of between about 1 km/hour (kilometer per hour) and about 5 km/hour (e.g., a general speed of 2 km/hour), a bicycle mode having a speed range of between about 5 km/hour and about 29 km/hour (e.g., a general speed of 6 km/hour), a car mode having a speed range of between about 50 km/hour and about 90 km/hour (e.g., a general speed of 60 km/hour), a ship mode having a speed range of between about 25 km/hour and about 50 km/hour (e.g., a general speed of 30 km/hour), a high-speed train mode having a speed range of between about 180 km/hour and about 350 km/hour (e.g., a general speed of 200 km/hour), an airplane mode having a speed range of between about 350 km/hour and about 950 km/hour (e.g., a general speed of 400 km/hour), and/or any other desired transportation mode.

At step 525, system 300 may operate to control accessory 315 based on the predetermined range or ranges into which the motion data may fall (e.g., determined at step 520). For example, if the sensed motion data may be within (e.g., the motion amplitude falls within) a given predetermined range of the plurality of predetermined ranges, system 300 may control accessory 315 and/or accessory 308 (e.g., an adult toy) to perform a predetermined action or function (e.g., predefined act) depending on a level or an amount of the motion data. Controller 319 may control motor 316 to actuate and/or cause accessory 315 (e.g., and/or accessory 308) to perform the predetermined action or function at a desired level or intensity. The predetermined action or function may include accessory 315 operating to sexually stimulate model 325 (e.g., an operator of accessory 315 that may be an adult toy). The predetermined action or function corresponding to the predetermined range may include accessory 315 (e.g., and/or accessory 308) vibrating at a desired level or strength, accessory 315 (e.g., and/or accessory 308) performing a suction operation at a desired level or strength, accessory 315 (e.g., and/or accessory 308) rotating or swinging at a desired speed or amount, accessory 315 (e.g., and/or accessory 308) emitting heat at a desired level or strength, accessory 315 (e.g., and/or accessory 308) contracting or expanding by a desired amount, and/or any other suitable action or function. User 320 may view the operation of accessory 315 (e.g., and/or accessory 308) operated by model 325 or user 320 via an operation of user device 305, model device 310, network 330, and/or any other suitable components of system 300.

At step 525 and in at least some exemplary embodiments, controller 319 may control motor 316 to actuate or cause accessory 315 (e.g., and/or accessory 308) to increase or decrease a level or intensity of the predetermined action or function based on the predetermined range identified at step 520. For example as a value (e.g., a speed) of the predetermined range increases (e.g., increasing from a car mode to an airplane mode), controller 319 may cause motor 316 to actuate or cause accessory 315 (e.g., and/or accessory 308) to increase a level or intensity of the predetermined action or function. As a value of the predetermined range decreases, controller 319 may cause motor 316 to actuate or cause accessory 315 (e.g., and/or accessory 308) to decrease a level or intensity of the predetermined action or function. For example, motor 316 may be controlled by controller 319 to vibrate accessory 315 (e.g., and/or accessory 308) at an increased or a decreased level or strength (e.g., intensity), perform a suction operation at an increased or a decreased level or strength (e.g., intensity), rotate or swing accessory 315 (e.g., and/or accessory 308) at an increased or a decreased level or strength (e.g., intensity), contract or expand accessory 315 (e.g., and/or accessory 308) by an increased or a decreased amount, increase or decrease a temperature or an amount of heat emitted from accessory 315 (e.g., and/or accessory 308), and/or cause accessory 315 and/or accessory 308 to perform any other suitable action or function at an increased or a decreased level or strength (e.g., intensity). Motor 316 may also be controlled directly by any other suitable component of system 300 (e.g., user device 305, network 330, or model device 310) for example via communication device 318.

In at least some exemplary embodiments, as motion data sensed and transferred at step 515 increases (e.g., a velocity and/or acceleration of user device 305 increases), controller 319 may cause motor 316 to actuate or cause accessory 315 (e.g., and/or accessory 308) to increase a level or intensity of the predetermined action or function at step 525 based on the determination at step 520. As motion data sensed and transferred at step 515 decreases (e.g., a velocity and/or acceleration of user device 305 decreases), controller 319 may cause motor 316 to actuate or cause accessory 315 (e.g., and/or accessory 308) to decrease a level or intensity of the predetermined action or function at step 525 based on the determination at step 520.

In at least some exemplary embodiments, if a reward (e.g., a tip) falls within one or more predetermined ranges of rewards, controller 319 may cause motor 316 to actuate or cause accessory 315 (e.g., and/or accessory 308) to operate at a level or intensity of the predetermined action or function corresponding to the predetermined range of rewards. For example, controller 319 may cause motor 316 to actuate accessory 315 (e.g., an adult toy) to perform the predetermined action or function based on an amount of said reward (e.g., at a predetermined intensity corresponding to the reward) to sexually stimulate model 325 operating accessory 315 (e.g., and/or user 320 operating accessory 308).

In at least some exemplary embodiments, accessory 315 (e.g., and/or accessory 308) may be connected by the exemplary disclosed short range communication techniques to user device 305 and operated by user 320. Model 325 may control an operation of accessory 315 (e.g., and/or user 320 may control accessory 308) via model device 310, network 330, and user device 305 similarly to as described above.

At step 530, system 300 may determine whether or not motion data sensing is to continue based on, for example, input provided by user 320, a predetermined operation or algorithm of the exemplary disclosed module, and/or any other suitable criteria. If motion data sensing is to continue, system 300 may return to step 515. System 300 may repeat steps 515 through 530 for any desired number of iterations. If motion data sensing is not to continue, system 300 may proceed to step 535.

At step 535, system 300 may determine whether or not system 300 is to be reconfigured based on, for example, input provided by user 320, a predetermined operation or algorithm of the exemplary disclosed module, and/or any other suitable criteria. If system 300 is to be reconfigured, system 300 may return to step 510. System 300 may repeat steps 510 through 535 for any desired number of iterations. If system 300 is not to be reconfigured, system 300 may proceed to step 540, at which process 500 ends.

The exemplary disclosed system may operate for example as described herein based on motion data provided by sensor array 306 of user device 305. The exemplary disclosed system may also operate for example similarly to as described herein based on motion data provided by sensor array 306 of model device 310.

In at least some exemplary embodiments, the exemplary disclosed system, apparatus, and method may include using sensor array 306 of user device 305 (e.g., and/or model device 310) to obtain motion data (e.g., a mobile phone's own acceleration sensor and GPS to obtain a moving speed or acceleration), and transferring and using the moving speed or acceleration to determine a certain value (e.g., a strength data) by the exemplary disclosed algorithms. The strength value may be transmitted to accessory 315 and/or accessory 308 (e.g., a toy) via Bluetooth® or any other suitable technique, which may be analyzed by the toy (e.g., controller 319 and/or any other suitable component of system 300 using the exemplary disclosed module) and converted into a vibration intensity of motor 316 (e.g., the toy motor), so as to product (e.g., realize) the toy vibration based on the user's device movement synchronization.

In at least some exemplary embodiments, system 300 may operate using a control pattern. The control pattern may include at least one instruction signal set that may actuate accessory 308 and/or 315 (e.g., a sexual stimulation device) to sequentially perform one or more series of different predefined acts and/or different levels of the one or more predefined acts, wherein a given type or kind of predefined act or a given level of the predefined act may correspond to a given instruction signal. Different instruction signals together may comprise an instruction signal set. The instruction signals may be configured to cause customization of the predefined act such as, for example, vibration, rotation, swinging, inhalation, temperature variation, expansion, suction, and contraction of the adult toy. Different levels of the predefined act may include amplitude, frequency, acceleration, temperature, periodicity, and/or duration.

Figure 5:
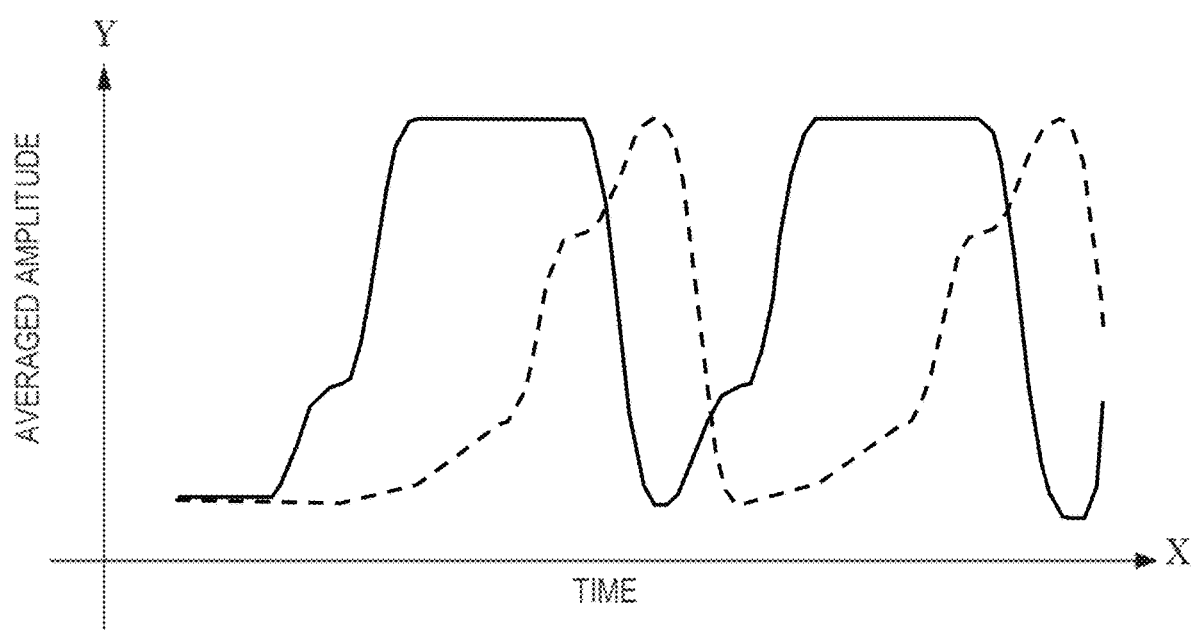
FIG. 5 is a chart illustration, in accordance with an example embodiment of the present disclosure.

FIG. 5 illustrates exemplary embodiments of the exemplary disclosed control pattern. The exemplary disclosed control pattern may include one or a plurality of control signals. The at least one instruction signal set may actuate the exemplary disclosed sexual stimulation device (e.g., adult toy) to sequentially perform one or more series of predefined acts (e.g., different predefined acts and/or different levels of one or more predefined acts and/or different accessories (e.g., different toys among a set of toys)). One type (e.g., kind) of the predefined act or one level of the predefined act may correspond to one instruction signal. Different instruction signals may together comprise the instruction signal set for example as illustrated in FIG. 5. The instruction signals may be configured to cause customization of the predefined act such as, for example, vibration, rotation, swinging, inhalation, temperature variation, temperature control, stretching, reciprocation, expansion, suction, bending, and/or contraction of the adult toy. Different levels of operation of the exemplary disclosed accessory while performing the predefined act may include different levels of amplitude, frequency, acceleration, temperature, periodicity, and/or duration.

In at least some exemplary embodiments and for example as illustrated in FIGS. 6A, 6B, 7, and 8, system 300 may control devices (e.g., one or more accessories 308 and/or 315) based on a distance between devices (e.g., one or more viewer accessories 308, one or more model accessories 315, one or more user devices 305, and/or one or more model devices 310). For example, a smart toy (e.g., one or more accessories 308 and/or 315) may be wirelessly controlled based on a distance between that smart toy and another device (e.g., one or more viewer accessories 308, one or more model accessories 315, one or more user devices 305, and/or one or more model devices 310), which may provide enjoyment for single user or multiple users. System 300 may operate in a plurality of modes (e.g., solo mode, acquaintance mode, stranger mode, online game mode, and/or any other suitable mode) for example as described herein. For example in a solo mode, a user may use system 300 by himself or herself. For example in a solo mode, the exemplary disclosed accessory (e.g., adult toy) and user device may belong to the same user, with the user controlling different levels of operation or action of the adult toy by holding the user device closer to and/or further away from the adult toy during use. Also in at least some exemplary embodiments, system 300 may or may not involve an online broadcast and/or streaming (e.g., across a broadcast area). For example, different viewers tipping a model online may trigger different intensities of the model's exemplary disclosed accessory (e.g., sex toy) according to any desired distance (e.g., a distance between the viewer's IP address and the model's IP address). In at least some exemplary embodiments, users may be strangers, acquaintances, friends, or any other desired relationship.

Figure 6A:
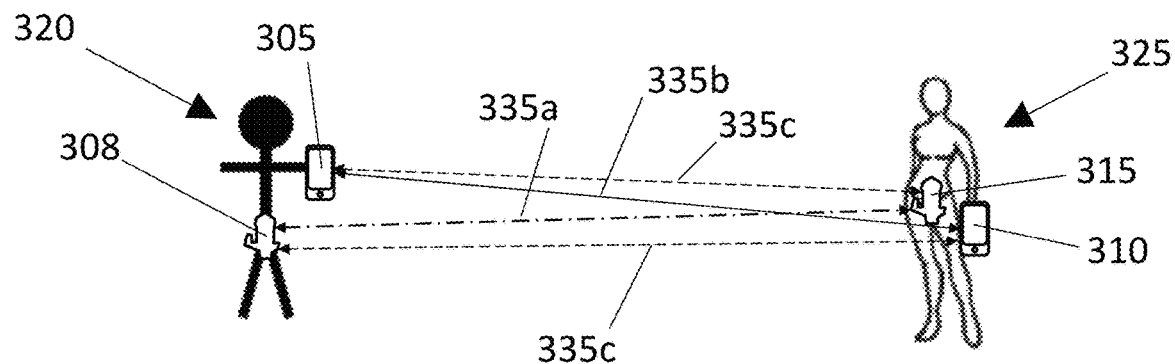
FIG. 6A is a schematic illustration of an exemplary system of the present invention.
Figure 6B:
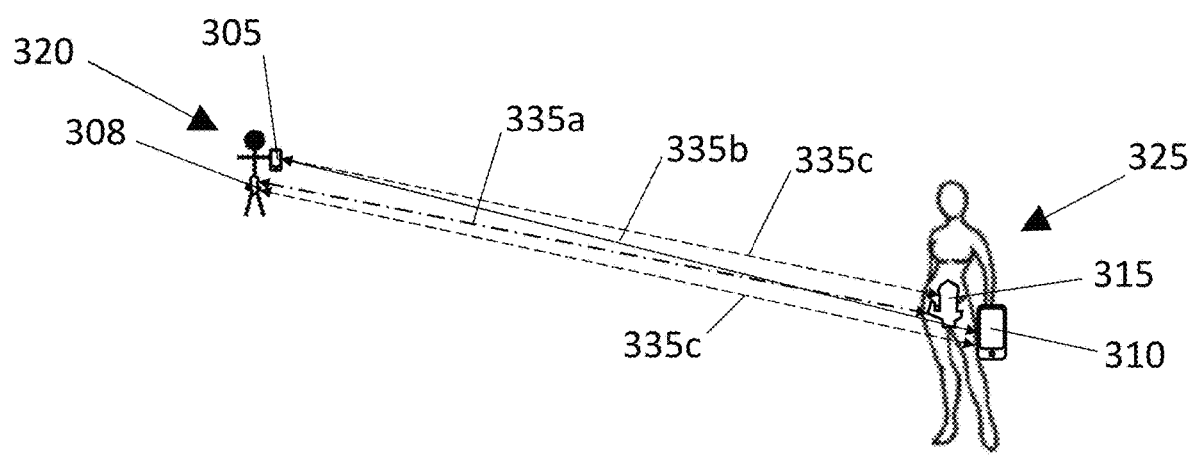
FIG. 6B is a schematic illustration of an exemplary system of the present invention.

As illustrated in FIGS. 6A and 6B, users (e.g., one or more users 320 and/or one or more models 325) may be located at any desired distance from each other during an operation of system 300. The exemplary disclosed users may be located at a distance relative to each other at any desired location such as, for example, in public, on a sidewalk, in a public or private park, in a recreation area, in a mall, at a sporting event, at any desired public or private place, and/or any desired location. For example, a user A (e.g., user 320) and/or a user B (e.g., user 325) may be located a few feet from each other, several hundred feet from each other, up to a mile from each other, or several miles or more from each. Any suitable technique may be used to determine a distance (e.g., a physical distance) between users (e.g., users 320 and/or models 325) such as, for example, ultrasonic detection, UWB positioning, Bluetooth® positioning, Wi-Fi positioning, satellite positioning using any suitable technique (e.g., GPS, Beidou™, Galileo™, GLONASS™, and/or any other suitable global navigation system), RFID positioning, base station positioning, and/or any other suitable technique. For example, components of viewer accessory 308, model accessory 315, user device 305, and/or model device 310 may operate to determine a distance between users 320 and/or models 325 based on determining a distance between viewer accessory 308, model accessory 315, user device 305, model device 310, and/or directly between bodies of users 320 and/or models 325. For example, system 300 may operate to determine a distance 335a between accessories (e.g., accessories 308 and/or 315 such as adult toys) of different users, a distance 335b between user devices (e.g., user devices 305 and/or model devices 310 such as smartphones, tablets, computers, virtual reality devices, and/or other computing devices) of different users, and/or a distance 335c between accessories (e.g., accessories 308 and/or 315 such as adult toys) and user devices (e.g., user devices 305 and/or model devices 310 such as smartphones, tablets, computers, virtual reality devices, and/or other computing devices) of different users.

The exemplary disclosed system may include a terminal device (e.g., viewer accessory 308, model accessory 315, user device 305, and/or model device 310). The terminal device may be a smart device. The terminal device may communicate with one or more adult toys (e.g., accessories 308 and/or 315) via Bluetooth®, Wi-Fi, RFID, GPS, Beidou™, UWB (Ultra Wide Band), and/or any other suitable communication technique such as any desired wireless techniques.

As illustrated in FIGS. 6A and 6B, distances 335a, 335b, and 335c may vary based on a relative position of users. For example, users may move closer together or toward each other (e.g., movement from FIG. 6B to FIG. 6A) and/or users may move away from each other (e.g., movement from FIG. 6A to FIG. 6B). Accordingly, distances 335a, 335b, and 335c may increase or decrease based on movement (e.g., relative movement) of users. For example, a physical distance between two users (e.g., user A that may be user 305 and user B that may be model 310) may be determined by system 300 based on a distance between a toyA—toyB (e.g., distance 335a), between a toyA— phoneB (e.g., distance 335c), between a phoneA (connected to toyA)—toyB (e.g., distance 335c), phoneA (connected to toyA)—phoneB (e.g., distance 335b), and/or phoneA (connected to toyA)—phoneB (connected to toyB) (e.g., distance 335b). For example, the exemplary disclosed distances may be calculated based on an actual position of user accessories and/or devices, a relative distance between accessories and/or devices of different users without identifying their positions, and/or any other suitable technique.

Figure 7:
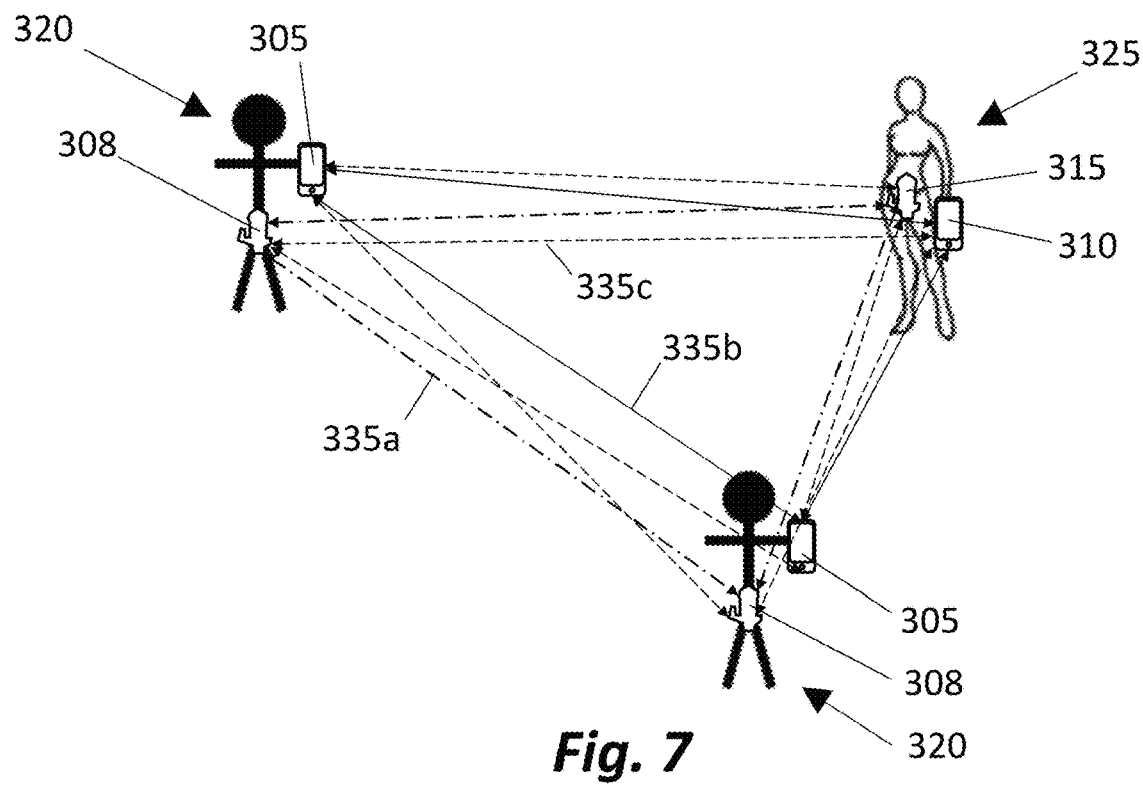
FIG. 7 is a schematic illustration of an exemplary system of the present invention.

As illustrated in FIG. 7, system 300 may operate to determine distances 335a, 335b, and/or 335c between any desired plurality of users (e.g., 3 or more users, including for example dozens or more users). For example, distances 335a, 335b, and/or 335c may be determined between any desired number of suitable devices (e.g., viewer accessories 308, model accessories 315, user devices 305, and/or model devices 310).

System 300 may control devices such as adult toys (e.g., accessories 308 and/or 315) based on distances 335a, 335b, and/or 335c. For example, system 300 may control accessories 308 and/or 315 based on variation of distances 335a, 335b, and/or 335c including an increase and/or a decrease of distances 335a, 335b, and/or 335c. Based on an increase and/or a decrease of distances 335a, 335b, and/or 335c, system 300 may control accessories 308 and/or 315 (e.g., an adult toy) to perform a predetermined action (e.g., predefined act) such as a mechanical action for sexually stimulating a user of the adult toy. Based on an increase and/or a decrease of distances 335a, 335b, and/or 335c, system 300 may control accessories 308 and/or 315 to operate at a relatively higher or lower level (e.g., as the distance increases then the level increases, or as the distance decreases then the level decreases). For example, a level (e.g., amplitude, frequency, speed, acceleration, temperature, number of reciprocation, and/or duration) of vibration, rotation, suction, contraction, expansion, temperature control, and/or reciprocating movement may be increased or decreased based on variation of distances 335a, 335b, and/or 335c. The various exemplary disclosed mechanical actions may correspond to any suitable driving unit that may be included in the exemplary disclosed accessories (e.g., accessories 308 and/or 315 such as adult toys) such as, for example, a vibration motor, a rotor motor, a heating unit, an air valve unit, a reciprocating unit, and/or any other suitable driving unit.

System 300 may operate using determined distances 335a, 335b, and/or 335c in any desired mode. For example, system 300 may operate in a first mode (e.g., an acquaintance mode) in which a first accessory (e.g., an adult toy of a first user) may be matched to a second accessory and/or a second user device of a second user. Devices may be matched based on pairing or any other suitable technique using any suitable communication techniques such as the exemplary disclosed communication techniques. System 300 may control an accessory to operate at a higher level (e.g., or a lower level) when the users are closer or move closer, and at a weaker level (e.g., or a higher level) when the two users are further apart or move away from each other.

System 300 may also operate in a second mode (e.g., a stranger mode) in which a first accessory (e.g., an adult toy of a first user) and a second accessory and/or a second user device of a second user may be utilized. In at least some exemplary embodiments in stranger mode, users may wear accessories (e.g., accessories 308 and/or 315 such as adult toys) discreetly such as, for example, under their clothes. The users may be in any suitable location such as outside on the street, or in a public place such as a shopping area, park, or recreation area (e.g., and/or other exemplary disclosed area for example as described herein). Users may have utilized user devices (e.g., devices 305 and/or 325 and/or accessories 308 and/or 315) to activate the exemplary disclosed stranger mode. When distances 335a, 335b, and/or 335c fall below any desired distance (e.g., a predetermined or selected distance that may be any suitable distance such as 100 meters and/or any other desired distance) and/or the distance varies at any suitable or predetermined rate (e.g., users near each other at a relatively quick rate), then system 300 may control an operation of user accessories (e.g., accessories 308 and/or 315). For example, system 300 may control an accessory of one or more users that may be located relatively close to each other to operate at a higher level (e.g., or a weaker or lower level) when the users are closer or move closer, and/or at a weaker or lower level (e.g., or a higher level) when the users are further apart or move away from each other. Any suitable settings or parameters may be used in stranger mode such as designating one user as a pursuer or chaser and another user as being chased (e.g., as the pursuer nears the chased user, system 300 controls the chased user's accessory to operate at an increasing or decreasing level such as increasing or decreasing vibration intensity). Any suitable game or settings may be used based for example on varying distances 335a, 335b, and/or 335c.

In at least some exemplary embodiments in the second mode (e.g., stranger mode), system 300 may control one or more accessories (e.g., sex toys) according to a control pattern preset by the stranger similar to for example as described regarding FIG. 5. System 300 may also control one or more accessories based on direct control by a user (e.g., the stranger) in real-time or near real-time via the stranger's device (e.g., device 305 or 310 such as a phone). For example, a control panel of a graphical user interface of the user's (e.g., stranger's) device may be used for controlling a toy of another user in stranger mode (e.g., based on distances 335a, 335b, and/or 335c being above or below a predetermined distance and/or within a desired range). In at least some exemplary embodiments, a control panel may be displayed (e.g., shown and called out) on a GUI of a user's (e.g., userB's) user device, when a distance between another user's (e.g., userA's) adult toy (e.g., and/or userA's user device connected thereto) and userB's device meets a threshold (e.g., the exemplary disclosed distance for example as described herein). If the users find the interaction or game to be enjoyable, the users can "friend" each other via the exemplary disclosed modules and application using their respective user devices (e.g., devices 305 and/or 310). System 300 may serve as a social network in which users who meet in stranger mode may connect and meet each other in person based on interaction using system 300.

Figure 8:
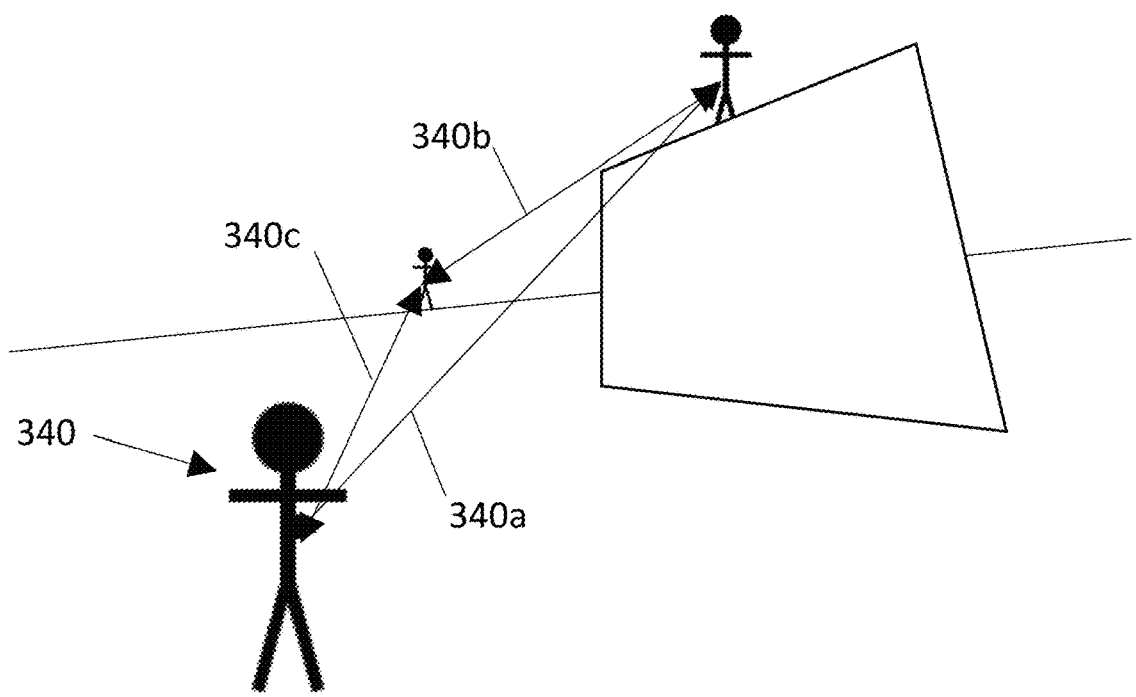
FIG. 8 is a schematic illustration of an exemplary system of the present invention.

System 300 may also operate in a third mode (e.g., an online game mode) for example as illustrated in FIG. 8. The third mode may occur in a virtual world, video game, or other computer-based setting. System 300 may determine virtual distances (e.g., virtual distances 340a, 340b, and/or 340c) between virtual objects 340. Virtual objects 340 may be video game characters or objects, avatars, virtual objects (e.g., terminal devices), and/or any other suitable virtual objects or features. System 300 may determine virtual distances (e.g., virtual distances 340a, 340b, and/or 340c) by calculating the virtual distance between a first virtual coordinate set of a first object (e.g., a first virtual object 340) and a second virtual coordinate set of a second object (e.g., a second virtual object 340) in a virtual world (e.g., or between any desired number of virtual objects 340). For example, although two actual physical users and accessories (e.g., toys) of two users may be distanced hundreds or thousands of miles apart in the real world (e.g., according to their IP address), their respective game characters (e.g., virtual objects 340) may be moved by a user's remote, keyboard/mouse, VR controller, buttons or sensor(s) on a sex toy of the user, and/or any other suitable technique. The virtual distance (e.g., virtual distance 340a, 340b, and/or 340c) may be any suitable distance (e.g., 10 meters apart) in a virtual world or environment. System 300 may thereby determine the virtual distance (e.g., virtual distance 340a, 340b, and/or 340c) such as, for example, 10 meters or any other suitable distance. System 300 may control the actual physical accessories (e.g., accessories 308 and/or 315) based on variation of virtual distances 340a, 340b, and/or 340c similarly to as described above regarding distances 335a, 335b, and/or 335c. In at least some exemplary embodiments, the exemplary disclosed distances (e.g., distances 335a, 335b, 335c, 340a, 340b, and/or 340c) may include physical distances between physical devices, virtual distances between virtual devices, distances between IP address locations, and/or distances between an IP address location and a physical device.

Figure 9:
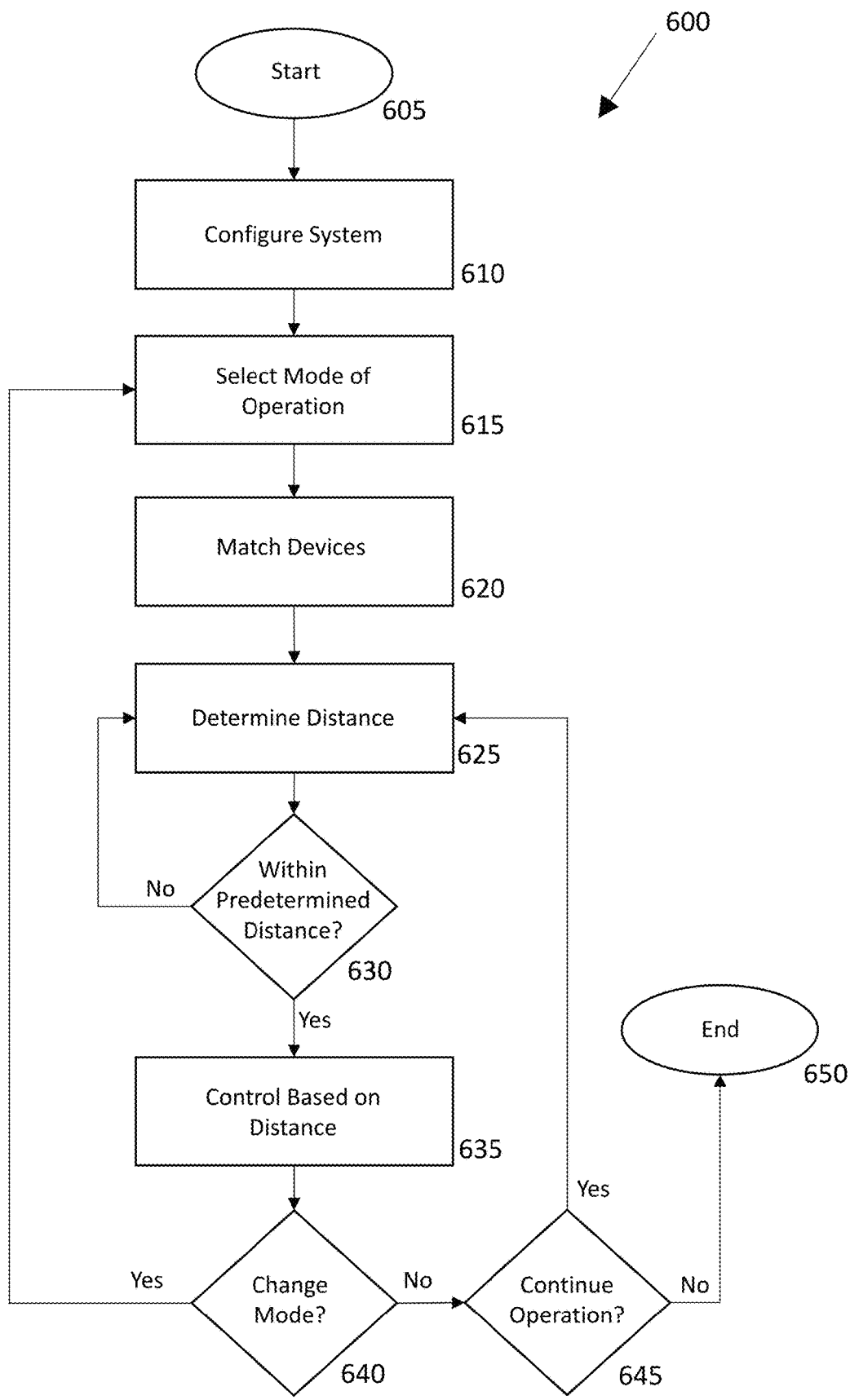
FIG. 9 is a flowchart showing an exemplary process of the present invention.

An exemplary operation of the exemplary disclosed system, apparatus, and method will now be described. For example, FIG. 9 illustrates an exemplary process 600 of system 300. Accessories 308 and/or 315 may be controlled to perform mechanical actions in process 600 similarly to as described above regarding process 500. Process 600 begins at step 605.

At step 610, system 300 may be configured similarly to as described at step 510 of process 500. At step 615, a mode of operation (e.g., acquaintance mode, stranger mode, online game mode, or any other desired mode) may be selected based on input provided by a user, a predetermined operation or algorithm of the exemplary disclosed module, and/or any other suitable criteria.

At step 620, devices may be matched if applicable for the selected mode. For example if acquaintance mode was selected at step 615, a first accessory (e.g., an adult toy of a first user such as user 320 or model 325) may be matched to a second accessory and/or a second user device of a second user. Also for example, a second accessory of the second user may be matched to the first accessory and/or the first user device of the first user. Any desired number of devices may be matched (e.g., including matching two, three, or more devices together) for example as illustrated in FIG. 7. If matching of devices is not involved in a selected mode (e.g., stranger mode or online game mode), process 600 may proceed directly from step 615 to step 625.

Returning to FIG. 9, at step 625 system 300 may operate to determine distance. For example, system 300 may operate to determine distances (e.g., distances 335a, 335b, 335c, 340a, 340b, and/or 340c) depending on the selected mode for example as described above.

At step 630, system 300 may operate to determine whether a given user device and/or accessory of a first user (e.g., user 320 or model 325) are within a predetermined distance or distance range of another user device and/or accessory of a second user (e.g., or user devices and/or accessories of a plurality of users). Step 630 may occur in some or all modes (e.g., stranger mode) or may not occur in some modes (e.g., acquaintance mode, in which process 600 may proceed directly from step 625 to step 635). For example, system 300 may operate to determine whether determined distances (e.g., distances 335a, 335b, 335c, 340a, 340b, and/or 340c) are greater or less than a predetermined distance and/or fall within one or more predetermined ranges of distances. If system 300 determines that the determined distances do not meet or exceed a predetermined threshold or do not fall within a predetermined range of values, process 600 may return to step 625. If system 300 determines that the determined distances meet or exceed a predetermined threshold value and/or fall within a predetermined threshold range of values, process 600 may proceed to step 635.

At step 635, system 300 may operate to control accessories of one or more users (e.g., accessories 308 and/or 315) who may be within the predetermined distance and/or ranges determined at step 630 (e.g., and/or during certain modes such as acquaintance mode). Based on the exemplary disclosed determined distances (e.g., distances 335a, 335b, 335c, 340a, 340b, and/or 340c) increasing, decreasing, meeting or exceeding a predetermined threshold value, falling within a predetermined range of threshold values, and/or increasing or decreasing at a relatively fast or slow rate, system 300 may control accessories 308 and/or 315 to operate (e.g., perform a mechanical action and/or other exemplary disclosed action) at a relatively higher or lower level (e.g., as the distance increases then the level increases, or as the distance decreases then the level decreases). For example, a level (e.g., amplitude, frequency, speed, acceleration, temperature, number of reciprocation, and/or duration) of vibration, rotation, suction, contraction, expansion, temperature control, and/or reciprocating movement may be increased or decreased based on variation of the exemplary disclosed determined distances (e.g., distances 335a, 335b, 335c, 340a, 340b, and/or 340c). Also for example, if variation of the exemplary disclosed determined distances (e.g., distances 335a, 335b, 335c, 340a, 340b, and/or 340c) indicate relatively high or low velocity or acceleration (e.g., rate of change of distance or velocity), system 300 may operate to control the exemplary disclosed accessories to operate (e.g., perform a mechanical action or other exemplary disclosed action) at a relatively high or low level. System 300 may control the exemplary accessories in any desired manner based on values and/or variations of the exemplary disclosed determined distances (e.g., distances 335a, 335b, 335c, 340a, 340b, and/or 340c).

In at least some exemplary embodiments, changing the level of the exemplary disclosed predetermined action (e.g., mechanical action) based on a change of the exemplary disclosed distance (e.g., distance 335a, 335b, 335c, 340a, 340b, and/or 340c) may include adjusting the level to a first adjusted value that is equal to a value of the distance multiplied by a predetermined weight value (e.g., any suitable value for providing a desired level of mechanical action by the exemplary disclosed accessory). Changing the level of the exemplary disclosed predetermined action (e.g., mechanical action) based on a change of the exemplary disclosed distance (e.g., distance 335a, 335b, 335c, 340a, 340b, and/or 340c) may also include adjusting the level to a second adjusted value that is equal to an initial value of the level plus a multiplied value that may be a change of the distance multiplied by an adjustment weight value (e.g., any suitable value for providing a desired level of mechanical action by the exemplary disclosed accessory).

In at least some exemplary embodiments, as a plurality of users are disposed relatively closely to each other or move relatively close to each other (e.g., move from the relative positions of FIG. 6B toward or to the relative positions of FIG. 6A), system 300 may operate to control one or more exemplary disclosed accessories (e.g., one or more accessories 308 and/or 315) to operate at an increasing (e.g., or decreasing) level as the exemplary disclosed distance (e.g., distances 335a, 335b, 335c, 340a, 340b, and/or 340c) decreases. Also for example, as a plurality of users are disposed relatively far from each other or move relatively far from each other (e.g., move from the relative positions of FIG. 6A toward or to the relative positions of FIG. 6B), system 300 may operate to control one or more exemplary disclosed accessories (e.g., one or more accessories 308 and/or 315) to operate at a decreasing (e.g., or increasing) level as the exemplary disclosed distance (e.g., distances 335a, 335b, 335c, 340a, 340b, and/or 340c) increases. For example, system 300 may control a first accessory to operate at a higher level (e.g., or a weaker or lower level) when two or more users are closer or move closer, or at a weaker or lower level (e.g., or a higher level) when the two or more users are further apart or move away from each other. System 300 may operate to change the level of the exemplary disclosed predetermined action (e.g., mechanical action) proportionally to a change of the exemplary disclosed distance (e.g., distance 335a, 335b, 335c, 340a, 340b, and/or 340c).

System 300 may control the exemplary disclosed accessories for any desired time period or time periods. For example, system 300 may control the exemplary disclosed accessories until a predetermined distance or range of values is no longer exceeded or met by the determined distances distance (e.g., distances 335a, 335b, 335c, 340a, 340b, and/or 340c), based on a predetermined time, based on user input (e.g., data or tips such as payment provided to system 300), and/or any other suitable criteria.

At step 640, system 300 may determine whether a mode of operation is to be changed based on input provided by a user, a predetermined operation or algorithm of the exemplary disclosed module, and/or any other suitable criteria. If a mode of operation is to be changed, process 600 may return to step 615. If a mode of operation is not to be changed, process 600 may proceed to step 645.

At step 645, system 300 may determine whether an operation of system 300 is to be continued based on input provided by a user, a predetermined operation or algorithm of the exemplary disclosed module, and/or any other suitable criteria. If operation is to be continued, process 600 may return to step 625. If an operation is not to be continued, process 600 may end at step 650.

In at least some exemplary embodiments, the exemplary disclosed system may include an accessory control module, comprising computer-executable code stored in non-volatile memory, a processor, an accessory (e.g., accessory 308 or 315) of a user, and a terminal device (e.g., accessory 308, accessory 315, device 305, or device 310). The accessory control module, the processor, the accessory, and the terminal device may be configured to determine a distance between the terminal device and either the accessory or a user device of the user, and control the accessory to perform a predetermined action for sexually stimulating the user based on the distance. The terminal device may be a second user device or a second accessory of a second user, the second accessory being for sexually stimulating the second user. Controlling the accessory to perform the predetermined action may include at least one of initiating control of the accessory to perform the predetermined action based on the distance falling within a threshold range or below a threshold value, or changing a level of the predetermined action based on a change of the distance. The level may be at least one selected from the group of amplitude, frequency, speed, acceleration, temperature, number of reciprocations, duration, and combinations thereof. Changing the level of the predetermined action based on the change of the distance may include at least one of adjusting the level to a first adjusted value that is equal to a value of the distance multiplied by a predetermined weight value, or adjusting the level to a second adjusted value that is equal to an initial value of the level plus a multiplied value that is a change of the distance multiplied by an adjustment weight value. Controlling the accessory to perform the predetermined action may further include at least one of controlling the accessory to perform the predetermined action based on a preset control pattern of the terminal device, or controlling the accessory to perform the predetermined action via the terminal device in real-time or near real-time. The accessory control module, the processor, the accessory, and the terminal device may be configured to send a user information of the terminal device to the user of the accessory. Controlling the accessory to perform the predetermined action may include at least one of decreasing a level of the predetermined action as the distance increases, or increasing the level of the predetermined action as the distance decreases. The predetermined action may be a mechanical action that is at least one selected from the group of vibration, rotation, suction, contraction, expansion, temperature control, reciprocating movement, and combinations thereof. The terminal device may be a smart device that communicates with the accessory via at least one selected from the group of Bluetooth®, Wi-Fi, RFID, GPS, Beidou™, Ultra Wide Band, and combinations thereof. The terminal device may be a second adult toy that communicates with the accessory that is a first adult toy via at least one of direct wireless communication or indirect wireless communication. The distance may be a physical distance and determining the physical distance may include calculating the physical distance according to at least one selected from the group of ultrasonic detection, UWB positioning, Bluetooth® positioning, Wi-Fi positioning, satellite positioning, RFID positioning, base station positioning and combinations thereof. The distance may be a virtual distance and determining the virtual distance may include calculating the virtual distance between a first virtual coordinate corresponding to the accessory and a second virtual coordinate corresponding to the terminal device in a virtual world. The accessory and the terminal device may be configured to wirelessly transmit and receive signals for determining the distance.

In at least some exemplary embodiments, the exemplary disclosed method may include providing an accessory (e.g., accessory 308 or 315) of a user, providing a terminal device (e.g., accessory 308, accessory 315, device 305, or device 310), wirelessly transmitting and receiving signals using the accessory and the terminal device, determining a distance between the terminal device and either the accessory or a user device of the user, and controlling the accessory to perform a predetermined action for sexually stimulating the user based on the distance. The exemplary disclosed method may also include changing a level of the predetermined action proportionally to a change of the distance. The level may be at least one selected from the group of amplitude, frequency, speed, acceleration, temperature, number of reciprocations, duration, and combinations thereof. The predetermined action may be a mechanical action that may be at least one selected from the group of vibration, rotation, suction, contraction, expansion, temperature control, reciprocating movement, and combinations thereof.

In at least some exemplary embodiments, the exemplary disclosed system may include an accessory control module, comprising computer-executable code stored in non-volatile memory, a processor, an adult toy (e.g., accessory 308 or 315) of a user, the adult toy configured to wirelessly receive or transmit signals, and a terminal device (e.g., accessory 308, accessory 315, device 305, or device 310) configured to wirelessly receive or transmit signals. The accessory control module, the processor, the adult toy, and the terminal device may be configured to determine a distance between the terminal device and either the adult toy or a user device of the user, control the adult toy to perform a mechanical action for sexually stimulating the user based on the distance, and change a level of the mechanical action proportionally to a change of the distance. Controlling the adult toy to perform the mechanical action may include initiating control of the adult toy to perform the mechanical action based on the distance falling within a threshold range or below a threshold value.

The exemplary disclosed system, apparatus, and method may provide an efficient and effective technique for controlling devices such as adult toys based on locations of users. For example, the exemplary disclosed system, apparatus, and method may control devices based on relative locations of users. In at least some exemplary embodiments, the exemplary disclosed system, apparatus, and method may control devices based on proximity of users to each other.

In at least some exemplary embodiments, the exemplary disclosed system, apparatus, and method may utilize sophisticated machine learning and/or artificial intelligence techniques to prepare and submit datasets and variables to cloud computing clusters and/or other analytical tools (e.g., predictive analytical tools) which may analyze such data using artificial intelligence neural networks. The exemplary disclosed system may for example include cloud computing clusters performing predictive analysis. For example, the exemplary neural network may include a plurality of input nodes that may be interconnected and/or networked with a plurality of additional and/or other processing nodes to determine a predicted result. Exemplary artificial intelligence processes may include filtering and processing datasets, processing to simplify datasets by statistically eliminating irrelevant, invariant or superfluous variables or creating new variables which are an amalgamation of a set of underlying variables, and/or processing for splitting datasets into train, test and validate datasets using at least a stratified sampling technique. The exemplary disclosed system may utilize prediction algorithms and approach that may include regression models, tree-based approaches, logistic regression, Bayesian methods, deep-learning and neural networks both as a stand-alone and on an ensemble basis, and final prediction may be based on the model/structure which delivers the highest degree of accuracy and stability as judged by implementation against the test and validate datasets.

Figure 10:
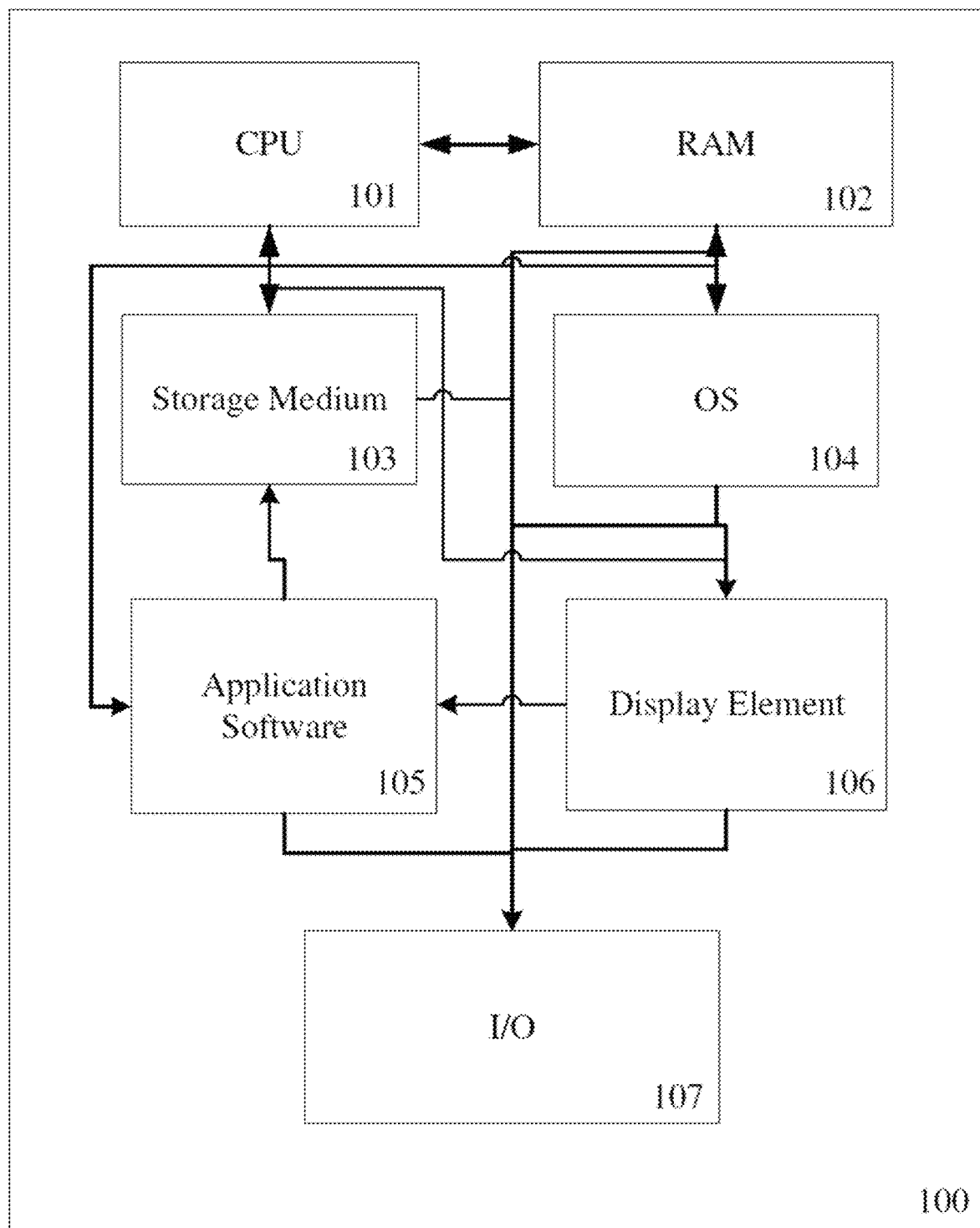
FIG. 10 is a schematic illustration of an exemplary computing device, in accordance with at least some exemplary embodiments of the present disclosure.

An illustrative representation of a computing device appropriate for use with embodiments of the system of the present disclosure is shown in FIG. 10. The computing device 100 can generally be comprised of a Central Processing Unit (CPU, 101), optional further processing units including a graphics processing unit (GPU), a Random Access Memory (RAM, 102), a mother board 103, or alternatively/additionally a storage medium (e.g., hard disk drive, solid state drive, flash memory, cloud storage), an operating system (OS, 104), one or more application software 105, a display element 106, and one or more input/output devices/means 107, including one or more communication interfaces (e.g., RS232, Ethernet, Wifi, Bluetooth®, USB). Useful examples include, but are not limited to, personal computers, smart phones, laptops, mobile computing devices, tablet PCs, touch boards, and servers. Multiple computing devices can be operably linked to form a computer network in a manner as to distribute and share one or more resources, such as clustered computing devices and server banks/farms.

Various examples of such general-purpose multi-unit computer networks suitable for embodiments of the disclosure, their typical configuration and many standardized communication links are well known to one skilled in the art, as explained in more detail and illustrated by FIG. 11, which is discussed herein-below.

According to an exemplary embodiment of the present disclosure, data may be transferred to the system, stored by the system and/or transferred by the system to users of the system across local area networks (LANs) (e.g., office networks, home networks) or wide area networks (WANs) (e.g., the Internet). In accordance with the previous embodiment, the system may be comprised of numerous servers communicatively connected across one or more LANs and/or WANs. One of ordinary skill in the art would appreciate that there are numerous manners in which the system could be configured and embodiments of the present disclosure are contemplated for use with any configuration.

In general, the system and methods provided herein may be employed by a user of a computing device whether connected to a network or not. Similarly, some steps of the methods provided herein may be performed by components and modules of the system whether connected or not. While such components/modules are offline, and the data they generated will then be transmitted to the relevant other parts of the system once the offline component/module comes again online with the rest of the network (or a relevant part thereof). According to an embodiment of the present disclosure, some of the applications of the present disclosure may not be accessible when not connected to a network, however a user or a module/component of the system itself may be able to compose data offline from the remainder of the system that will be consumed by the system or its other components when the user/offline system component or module is later connected to the system network.

Figure 11:
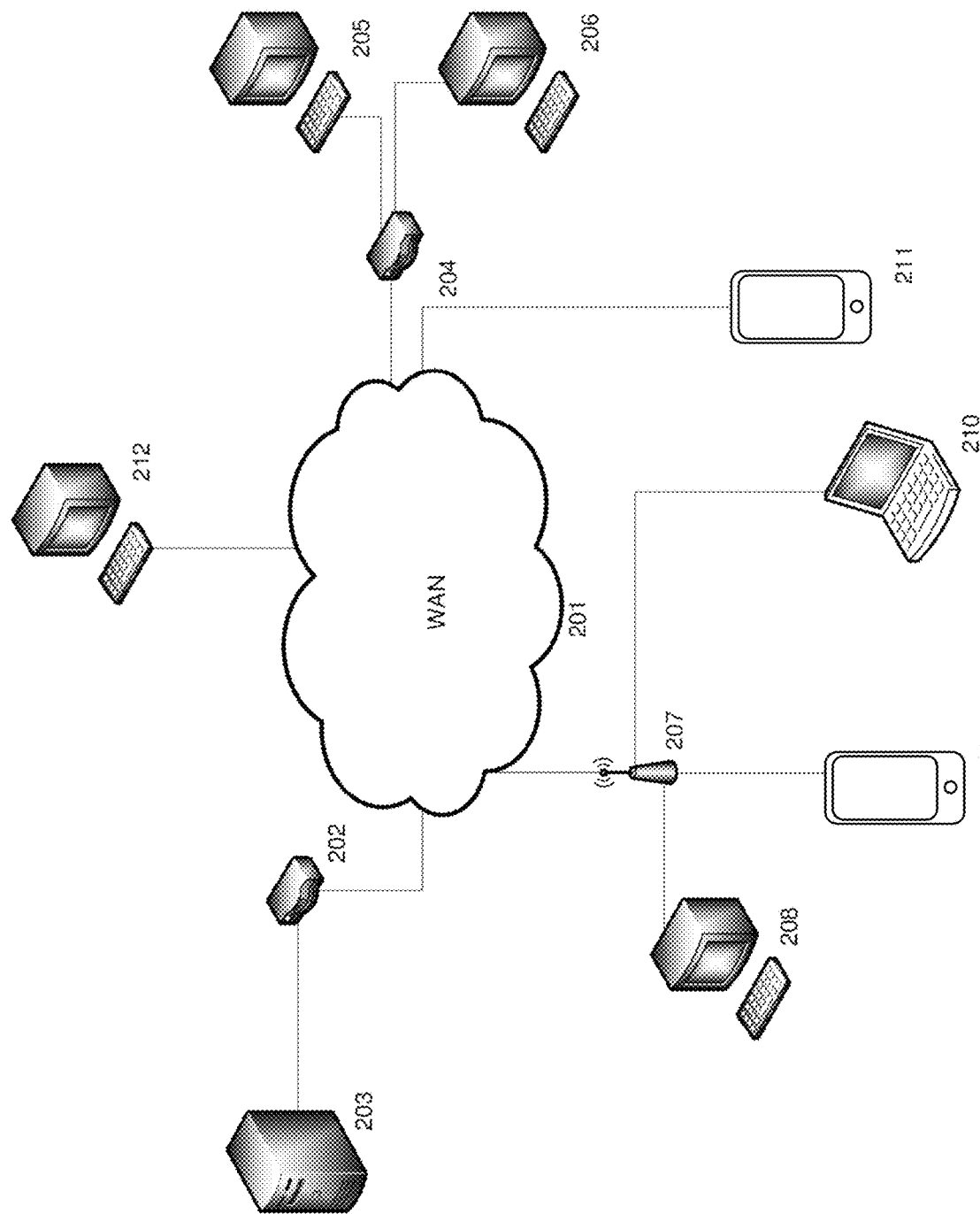
FIG. 11 is a schematic illustration of an exemplary network, in accordance with at least some exemplary embodiments of the present disclosure.

Referring to FIG. 11, a schematic overview of a system in accordance with an embodiment of the present disclosure is shown. The system is comprised of one or more application servers 203 for electronically storing information used by the system. Applications in the server 203 may retrieve and manipulate information in storage devices and exchange information through a WAN 201 (e.g., the Internet). Applications in server 203 may also be used to manipulate information stored remotely and process and analyze data stored remotely across a WAN 201 (e.g., the Internet).

According to an exemplary embodiment, as shown in FIG. 11, exchange of information through the WAN 201 or other network may occur through one or more high speed connections. In some cases, high speed connections may be over-the-air (OTA), passed through networked systems, directly connected to one or more WANs 201 or directed through one or more routers 202. Router(s) 202 are completely optional and other embodiments in accordance with the present disclosure may or may not utilize one or more routers 202. One of ordinary skill in the art would appreciate that there are numerous ways server 203 may connect to WAN 201 for the exchange of information, and embodiments of the present disclosure are contemplated for use with any method for connecting to networks for the purpose of exchanging information. Further, while this application refers to high speed connections, embodiments of the present disclosure may be utilized with connections of any speed.

Components or modules of the system may connect to server 203 via WAN 201 or other network in numerous ways. For instance, a component or module may connect to the system i) through a computing device 212 directly connected to the WAN 201, ii) through a computing device 205, 206 connected to the WAN 201 through a routing device 204, iii) through a computing device 208, 209, 210 connected to a wireless access point 207 or iv) through a computing device 211 via a wireless connection (e.g., CDMA, GMS, 3G, 4G) to the WAN 201. One of ordinary skill in the art will appreciate that there are numerous ways that a component or module may connect to server 203 via WAN 201 or other network, and embodiments of the present disclosure are contemplated for use with any method for connecting to server 203 via WAN 201 or other network. Furthermore, server 203 could be comprised of a personal computing device, such as a smartphone, acting as a host for other computing devices to connect to.

The communications means of the system may be any means for communicating data, including image and video, over one or more networks or to one or more peripheral devices attached to the system, or to a system module or component. Appropriate communications means may include, but are not limited to, wireless connections, wired connections, cellular connections, data port connections, Bluetooth® connections, near field communications (NFC) connections, or any combination thereof. One of ordinary skill in the art will appreciate that there are numerous communications means that may be utilized with embodiments of the present disclosure, and embodiments of the present disclosure are contemplated for use with any communications means.

Traditionally, a computer program includes a finite sequence of computational instructions or program instructions. It will be appreciated that a programmable apparatus or computing device can receive such a computer program and, by processing the computational instructions thereof, produce a technical effect.

A programmable apparatus or computing device includes one or more microprocessors, microcontrollers, embedded microcontrollers, programmable digital signal processors, programmable devices, programmable gate arrays, programmable array logic, memory devices, application specific integrated circuits, or the like, which can be suitably employed or configured to process computer program instructions, execute computer logic, store computer data, and so on. Throughout this disclosure and elsewhere a computing device can include any and all suitable combinations of at least one general purpose computer, special-purpose computer, programmable data processing apparatus, processor, processor architecture, and so on. It will be understood that a computing device can include a computer-readable storage medium and that this medium may be internal or external, removable and replaceable, or fixed. It will also be understood that a computing device can include a Basic Input/Output System (BIOS), firmware, an operating system, a database, or the like that can include, interface with, or support the software and hardware described herein.

Embodiments of the system as described herein are not limited to applications involving conventional computer programs or programmable apparatuses that run them. It is contemplated, for example, that embodiments of the disclosure as claimed herein could include an optical computer, quantum computer, analog computer, or the like.

Regardless of the type of computer program or computing device involved, a computer program can be loaded onto a computing device to produce a particular machine that can perform any and all of the depicted functions. This particular machine (or networked configuration thereof) provides a technique for carrying out any and all of the depicted functions.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Illustrative examples of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A data store may be comprised of one or more of a database, file storage system, relational data storage system or any other data system or structure configured to store data. The data store may be a relational database, working in conjunction with a relational database management system (RDBMS) for receiving, processing and storing data. A data store may comprise one or more databases for storing information related to the processing of moving information and estimate information as well one or more databases configured for storage and retrieval of moving information and estimate information.

Computer program instructions can be stored in a computer-readable memory capable of directing a computer or other programmable data processing apparatus to function in a particular manner. The instructions stored in the computer-readable memory constitute an article of manufacture including computer-readable instructions for implementing any and all of the depicted functions.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

The elements depicted in flowchart illustrations and block diagrams throughout the figures imply logical boundaries between the elements. However, according to software or hardware engineering practices, the depicted elements and the functions thereof may be implemented as parts of a monolithic software structure, as standalone software components or modules, or as components or modules that employ external routines, code, services, and so forth, or any combination of these. All such implementations are within the scope of the present disclosure. In view of the foregoing, it will be appreciated that elements of the block diagrams and flowchart illustrations support combinations of means for performing the specified functions, combinations of steps for performing the specified functions, program instruction technique for performing the specified functions, and so on.

It will be appreciated that computer program instructions may include computer executable code. A variety of languages for expressing computer program instructions are possible, including without limitation C, C++, Java, JavaScript, assembly language, Lisp, HTML, Perl, and so on. Such languages may include assembly languages, hardware description languages, database programming languages, functional programming languages, imperative programming languages, and so on. In some embodiments, computer program instructions can be stored, compiled, or interpreted to run on a computing device, a programmable data processing apparatus, a heterogeneous combination of processors or processor architectures, and so on. Without limitation, embodiments of the system as described herein can take the form of web-based computer software, which includes client/server software, software-as-a-service, peer-to-peer software, or the like.

In some embodiments, a computing device enables execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. The thread can spawn other threads, which can themselves have assigned priorities associated with them. In some embodiments, a computing device can process these threads based on priority or any other order based on instructions provided in the program code.

Unless explicitly stated or otherwise clear from the context, the verbs "process" and "execute" are used interchangeably to indicate execute, process, interpret, compile, assemble, link, load, any and all combinations of the foregoing, or the like. Therefore, embodiments that process computer program instructions, computer-executable code, or the like can suitably act upon the instructions or code in any and all of the ways just described.

The functions and operations presented herein are not inherently related to any particular computing device or other apparatus. Various general-purpose systems may also be used with programs in accordance with the teachings herein, or it may prove convenient to construct more specialized apparatus to perform the required method steps. The required structure for a variety of these systems will be apparent to those of ordinary skill in the art, along with equivalent variations. In addition, embodiments of the disclosure are not described with reference to any particular programming language. It is appreciated that a variety of programming languages may be used to implement the present teachings as described herein, and any references to specific languages are provided for disclosure of enablement and best mode of embodiments of the disclosure. Embodiments of the disclosure are well suited to a wide variety of computer network systems over numerous topologies. Within this field, the configuration and management of large networks include storage devices and computing devices that are communicatively coupled to dissimilar computing and storage devices over a network, such as the Internet, also referred to as "web" or "world wide web".

Throughout this disclosure and elsewhere, block diagrams and flowchart illustrations depict methods, apparatuses (e.g., systems), and computer program products. Each element of the block diagrams and flowchart illustrations, as well as each respective combination of elements in the block diagrams and flowchart illustrations, illustrates a function of the methods, apparatuses, and computer program products. Any and all such functions ("depicted functions") can be implemented by computer program instructions; by special-purpose, hardware-based computer systems; by combinations of special purpose hardware and computer instructions; by combinations of general purpose hardware and computer instructions; and so on—any and all of which may be generally referred to herein as a "component", "module," or "system."

While the foregoing drawings and description set forth functional aspects of the disclosed systems, no particular arrangement of software for implementing these functional aspects should be inferred from these descriptions unless explicitly stated or otherwise clear from the context.

Each element in flowchart illustrations may depict a step, or group of steps, of a computer-implemented method. Further, each step may contain one or more sub-steps. For the purpose of illustration, these steps (as well as any and all other steps identified and described above) are presented in order. It will be understood that an embodiment can contain an alternate order of the steps adapted to a particular application of a technique disclosed herein. All such variations and modifications are intended to fall within the scope of this disclosure. The depiction and description of steps in any particular order is not intended to exclude embodiments having the steps in a different order, unless required by a particular application, explicitly stated, or otherwise clear from the context.

The functions, systems and methods herein described could be utilized and presented in a multitude of languages. Individual systems may be presented in one or more languages and the language may be changed with ease at any point in the process or methods described above. One of ordinary skill in the art would appreciate that there are numerous languages the system could be provided in, and embodiments of the present disclosure are contemplated for use with any language.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

It will be apparent to those skilled in the art that various modifications and variations can be made to the disclosed system and method. Other embodiments will be apparent to those skilled in the art from consideration of the specification and practice of the disclosed method and apparatus. It is intended that the specification and examples be considered as exemplary only, with a true scope being indicated by the following claims.

What is claimed is:

1. A system, comprising:
   a memory device having stored thereon a set of instructions; and
   a processor configured to execute said set of instructions to:
      wirelessly transmit and receive signals using:
         an accessory of a user, wherein the accessory of a user is a sex toy of the user, and
         an electrical terminal device of a second user comprising a second user device communicatively connected to a second accessory of the second user, wherein the second user device is a second user personal computing device and the second accessory is a sex toy of the second user that is for sexually stimulating the second user;

determine a distance between the electrical terminal device and either the accessory or a first user device connected to the accessory, wherein the first user device is a first user personal computing device; and control the accessory to perform a predetermined action for sexually stimulating the user based on the distance;

wherein the distance is a virtual distance and determining the virtual distance includes calculating the virtual distance between a first virtual coordinate corresponding to the accessory and a second virtual coordinate corresponding to the electrical terminal device in a virtual world.

2. The system of claim 1, wherein the first user personal computing device and the second user personal computing device are smartphones.

3. The system of claim 1, wherein controlling the accessory to perform the predetermined action includes at least one of:

initiating control of the accessory to perform the predetermined action based on the distance falling within a threshold range or below a threshold value; or changing a level of the predetermined action based on a change of the distance.

4. The system of claim 3, wherein the level is at least one selected from the group of amplitude, frequency, speed, acceleration, temperature, number of reciprocations, duration, and combinations thereof.

5. The system of claim 3, wherein changing the level of the predetermined action based on the change of the distance includes at least one of:

adjusting the level to a first adjusted value that is equal to a value of the distance multiplied by a predetermined weight value; or adjusting the level to a second adjusted value that is equal to an initial value of the level plus a multiplied value that is a change of the distance multiplied by an adjustment weight value.

6. The system of claim 1, wherein controlling the accessory to perform the predetermined action further includes at least one of:

controlling the accessory to perform the predetermined action based on a preset control pattern of the electrical terminal device; or controlling the accessory to perform the predetermined action via the electrical terminal device in real-time or near real-time.

7. The system of claim 1, wherein the processor, the accessory, and the electrical terminal device are configured to send a user information of the electrical terminal device to the user of the accessory.

8. The system of claim 1, wherein controlling the accessory to perform the predetermined action includes at least one of:

decreasing a level of the predetermined action as the distance increases;

increasing the level of the predetermined action as the distance decreases;

decreasing a level of the predetermined action as the distance decreases; or increasing the level of the predetermined action as the distance increases.

9. The system of claim 1, wherein the predetermined action is a mechanical action that is at least one selected from the group of vibration, rotation, suction, contraction, expansion, temperature control, reciprocating movement, and combinations thereof.

10. The system of claim 1, wherein the electrical terminal device is a smart device that communicates with the accessory via at least one selected from the group of short distance communication, Wi-Fi, RFID, GPS, Ultra Wide Band, and combinations thereof.

11. The system of claim 1, wherein the electrical terminal device communicates with the accessory via at least one of direct wireless communication or indirect wireless communication.

12. The system of claim 1, wherein the distance is a physical distance and determining the physical distance includes calculating the physical distance according to at least one selected from the group of ultrasonic detection, UWB positioning, Wi-Fi positioning, satellite positioning, RFID positioning, base station positioning and combinations thereof.

13. The system of claim 1, wherein the accessory and the electrical terminal device are configured to wirelessly transmit and receive signals for determining the distance.

14. The system of claim 1, wherein the first user device and the second user device are selected from the group consisting of smartphones, tablets, and wearable devices.

15. The system of claim 1, wherein the first user device and the second user device are handheld devices.

* * * * *